(12) United States Patent
Heckel et al.

(10) Patent No.: US 10,221,202 B2
(45) Date of Patent: Mar. 5, 2019

(54) ANNELATED PHENOXYACETAMIDES

(71) Applicant: Boehringer Ingelheim International GmbH, Ingelheim am Rhein (DE)

(72) Inventors: Armin Heckel, Biberach an der Riss (DE); Dieter Hamprecht, Pozzolengo (IT); Joerg Kley, Mittelbiberach (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/654,301

(22) Filed: Jul. 19, 2017

(65) Prior Publication Data
US 2017/0313732 A1 Nov. 2, 2017

Related U.S. Application Data

(63) Continuation of application No. 15/241,150, filed on Aug. 19, 2016, now abandoned.

(60) Provisional application No. 62/207,405, filed on Aug. 20, 2015.

(51) Int. Cl.
| | | |
|---|---|---|
| C07F 9/6558 | (2006.01) |
| C07D 405/14 | (2006.01) |
| A61K 31/541 | (2006.01) |
| A61K 45/06 | (2006.01) |
| C07C 53/18 | (2006.01) |
| A61K 31/675 | (2006.01) |
| C07D 403/12 | (2006.01) |
| A61K 31/497 | (2006.01) |
| C07D 401/14 | (2006.01) |
| C07C 53/06 | (2006.01) |

(52) U.S. Cl.
CPC ........ C07F 9/65583 (2013.01); A61K 31/497 (2013.01); A61K 31/541 (2013.01); A61K 31/675 (2013.01); A61K 45/06 (2013.01); C07C 53/06 (2013.01); C07C 53/18 (2013.01); C07D 401/14 (2013.01); C07D 403/12 (2013.01); C07D 405/14 (2013.01)

(58) Field of Classification Search
CPC ...... C07F 9/65583; C07C 53/06; C07C 53/18
See application file for complete search history.

(56) References Cited

U.S. PATENT DOCUMENTS 9,126,985 B2 * 9/2015 Kley ................. C07D 405/14

FOREIGN PATENT DOCUMENTS

WO 2011079087 A1 6/2011

OTHER PUBLICATIONS

Venanzi, Journal of Medicinal Chemistry, Molecular Recognition of Amiloride Analogs, A molecular Electrostatic Potential Analysis, vol. 35, No. 9, 1992, p. 1643-1649.
Schoenberger, et al., Expert Opinion on Therapeutic Patents, Novel Small Molecule Epithelial Sodium channel inhibitors as potential therapeutics in cystic fibrosis—a patent evaluation, 23(10), 2013, p. 1383-1389.

* cited by examiner

Primary Examiner — Pancham Bakshi
(74) Attorney, Agent, or Firm — Philip I. Datlow

(57) ABSTRACT

The present invention relates to compounds of formula (I)

(I)

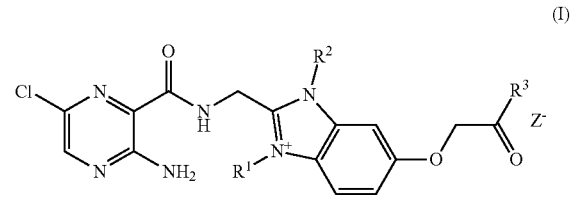

wherein $R^1$, $R^2$, $R^3$, and $Z^-$ have one of the meanings as indicated in the specification or a pharmaceutically acceptable salt thereof, to the use of compounds of formula (I) as a medicament, to pharmaceutical compositions comprising at least one compound of formula (I), as well as to medicament combinations containing one or more compounds of formula (I).

28 Claims, No Drawings

ANNELATED PHENOXYACETAMIDES

FIELD OF THE INVENTION

The present invention relates to compounds of formula (I)

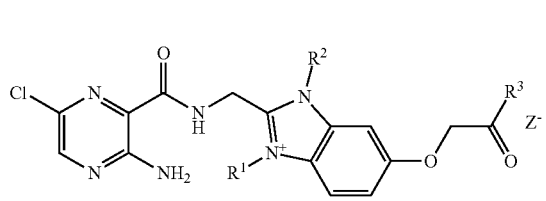

(I)

wherein $R^1$, $R^2$, $R^3$, and $Z^-$ have one of the meanings as indicated in the specification or a pharmaceutically acceptable salt thereof, to the use of compounds of formula (I) as a medicament, to pharmaceutical compositions comprising at least one compound of formula (I), as well as to medicament combinations containing one or more compounds of formula (I).

BACKGROUND TO THE INVENTION

WO2011079087, WO2015007516, WO2015007519, and WO2015007517 disclose amides of 3,5-diamino-6-halo-pyrazine-2-carboxylic acid of related structure showing ENaC (Epithelial Sodium Channel) inhibitor activity.

Venanzi teaches that the amino group in position 5 of the pyrazine moiety of amiloride and its analogs is essential for the stability of the blocking complex with ENaC (Venanzi et al., Journal of Medicinal Chemistry, 1992, Vol. 35 (9), 1643-1649).

The problem of the present invention is to provide further compounds for therapeutic use for the treatment of pathophysiological processes treatable by the blockade of an epithelial sodium channel, particularly for the treatment of the lungs and airways.

Such compounds should be potent inhibitors of ENaC. Suitable $IC_{50}$ values determined in the Ussing Chamber assay are typically below 30 nM.

Additionally, such compounds should exhibit a low permeability which is beneficial for topical lung treatment. Suitable permeability values determined in the CALU-3 cells assay are typically below $6 \times 10^{-7}$ cm/s.

Additionally, such compounds should have high solubility in aqueous media which is beneficial for administration by inhalation of an aqueous solution. Suitable solubility values in aqueous buffer with a physiologically acceptable pH value are 2% or higher.

Additionally, such compounds should have high hydrolytic stability in aqueous media which is beneficial for administration by inhalation of an aqueous solution.

Additionally, such compounds should inhibit in vivo water resorption in the lung upon topical administration. Topical lung administration of pharmacologically active doses of the compounds of the present invention should not or only to a low extent increase plasma aldosterone levels.

Surprisingly, it has been found that the claimed 3-amino-6-chloro-pyrazine-2-carboxylic acid derivatives which do not possess an amino group in position 5 of the pyrazine moiety are potent ENaC inhibitors and further possess the additional characteristics outlined above.

DETAILED DESCRIPTION OF THE INVENTION

The present invention relates to compounds of formula (I),

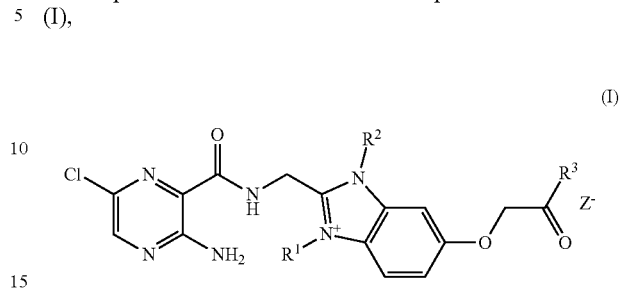

(I)

wherein $R^1$ and $R^2$ are independently selected from ethyl, 2-hydroxyethyl, 2-tetrahydrofuranylmethyl and 4-tetrahydropyranylmethyl;

$R^3$ is selected from a moiety $NR^aR^b$, wherein $R^a$ and $R^b$ are independently selected from hydrogen, $C_1$-$C_4$-alkyl and 1-(2-ethoxyethyl)piperidin-4-yl, wherein said $C_1$-$C_4$-alkyl may carry 1 or 2 substituents selected from hydroxyl, amino, $C_1$-$C_4$-alkylamino, di-$C_1$-$C_4$-alkylamino, (dimethylphosphinoyl)methoxy, 4-(dimethylphosphinoyl)phenyl, 6-methyl-3-hydroxy-pyridin-2-yl and the oxyanion of 6-methyl-3-hydroxy-pyridin-2-yl, provided that at least one of $R^a$ and $R^b$ is different from hydrogen, or wherein $R^a$ and $R^b$ together with the nitrogen they are attached to form a heterocyclic moiety selected from piperidine and 1-oxothiomorpholinyl, wherein the heterocyclic moiety may carry 1 or 2 substituents selected from $NH_2$; and $Z^-$ is selected from chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate and p-toluenesulfonate, or $Z^-$ may be absent if $R^a$ or $R^b$ is $C_1$-$C_4$-alkyl and carries the oxyanion of 6-methyl-3-hydroxy-pyridin-2-yl;

or a pharmaceutically acceptable salt thereof.

The compounds of formula (I) or the pharmaceutically acceptable salts thereof as defined herein are particularly suitable for the treatment of pathophysiological processes treatable by the blockade of an epithelial sodium channel, particularly for the treatment of the lungs and airways.

Accordingly the present invention further relates to compounds of formula (I) as defined herein or pharmaceutically acceptable salts thereof for use as a medicament.

The present invention further relates to compounds of formula (I) as defined herein or pharmaceutically acceptable salts thereof for use in the treatment of a disease selected from among respiratory diseases or complaints and allergic diseases of the airways.

The present invention further relates to compounds of formula (I) as defined herein or pharmaceutically acceptable salts thereof for use in the treatment of a disease selected from among chronic bronchitis, acute bronchitis, bronchitis caused by bacterial or viral infection or fungi or helminths, allergic bronchitis, toxic bronchitis, chronic obstructive pulmonary disease (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, and dry eyes.

The present invention further relates to a pharmaceutical composition comprising at least one compound of formula (I) as defined herein or pharmaceutically acceptable salts thereof and a pharmaceutically acceptable carrier.

The present invention further relates to medicament combinations containing besides one or more compounds of formula (I) as defined herein or pharmaceutically acceptable salts thereof, as further active substance one or more compounds selected from among the categories of further ENaC inhibitors, betamimetics, anticholinergics, corticosteroids, PDE4-inhibitors, LTD4-antagonists, EGFR-inhibitors, dopamine agonists, H1 antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the terminal term indicates the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

If a compound of the present invention is depicted in form of a chemical name and as a formula, in case of any discrepancy the formula shall prevail.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymously and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmacologically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a cationic group and optionally an additional basic or acidic moiety by conventional chemical methods. Generally, such salts can be prepared by reacting other salt forms of these compounds with a sufficient amount of the appropriate base or acid in water or in an organic diluent like ether, ethyl acetate, ethanol, isopropanol, or acetonitrile, or a mixture thereof. Moreover, counterions can generally be exchanged by ion exchange chromatography.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-4}$-alkyl, as used herein and in ther terms $C_{1-4}$-alkylamino and di-$C_{1-4}$-alkylamino, embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, and H$_3$C—C(CH$_3$)$_2$—.

In all cases of contradictions between structure and their naming, structure shall prevail.

PREFERRED EMBODIMENTS

One particular embodiment of the present invention relates to compounds of formula (I) or pharmaceutically acceptable salt thereof, wherein at least one of $R^1$ and $R^2$ is ethyl. Preferred are compounds of formula (I) or pharmaceutically acceptable salt thereof, wherein both of $R^1$ and $R^2$ are ethyl.

Another particular embodiment of the present invention relates to compounds of formula (I) or pharmaceutically acceptable salt thereof, wherein $R^1$ or $R^2$ is selected from 2-hydroxyethyl, (S)-2-tetrahydrofuranylmethyl, and 4-tetrahydropyranylmethyl.

Another particular embodiment of the present invention relates to compounds of formula (I) or pharmaceutically acceptable salts thereof, wherein $Z^-$ is selected from chloride, formate, and trifluoroacetate.

Another particular embodiment of the present invention relates to compounds of formula (I) or pharmaceutically acceptable salt thereof, wherein in $R^a$ or $R^b$ in the definition of $R^3$ is $C_1$-$C_4$-alkyl which carries 1 substituent selected from dimethylphosphinoylmethoxy and 4-(dimethylphosphinoyl)phenyl.

Another particular embodiment of the present invention relates to compounds of formula (I) or pharmaceutically acceptable salt thereof, carrying at least one primary or secondary amino group, i.e compounds of formula (I) or pharmaceutically acceptable salt thereof, wherein at least one of $R^a$ or $R^b$ in the definition of $R^3$ is $C_1$-$C_4$-alkyl, wherein $C_1$-$C_4$-alkyl carries at least one substituent selected from amino and $C_1$-$C_4$-alkylamino, or compounds of formula (I) or pharmaceutically acceptable salt thereof, wherein $R^a$ and $R^b$ in the definition of $R^3$ together with the nitrogen they are attached to are piperidine carrying 1 or 2 substituents selected from NH$_2$.

Another particular embodiment of the present invention relates to compounds of formula (I) or pharmaceutically acceptable salt thereof, wherein $R^a$ or $R^b$ in the definition of $R^3$ is $C_1$-$C_4$-alkyl carrying 6-methyl-3-hydroxy-pyridin-2-yl or the oxyanion of 6-methyl-3-hydroxy-pyridin-2-yl.

Preferred are compounds of formula (I) or the pharmaceutically acceptable salts thereof, wherein $R^3$ is selected from

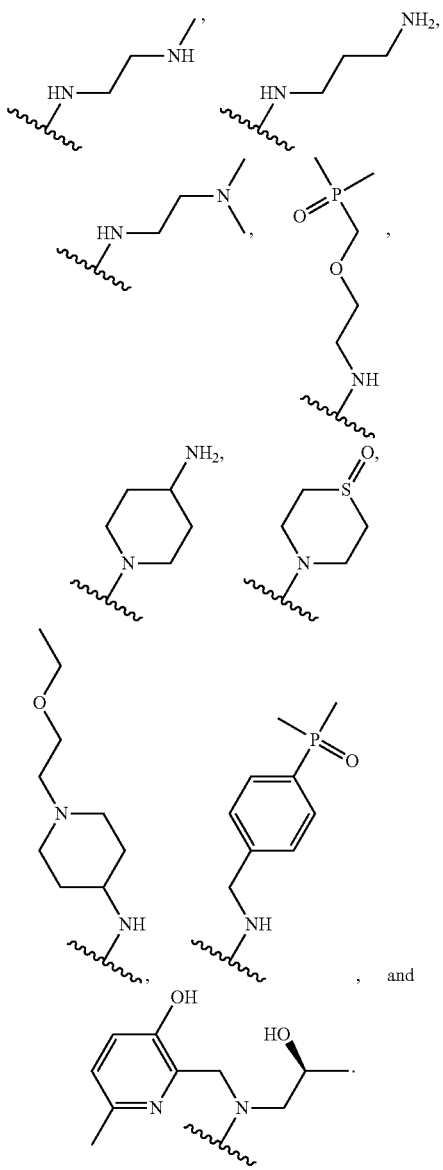

Another particular embodiment of the present invention relates to compounds of formula (I) or pharmaceutically acceptable salts thereof, selected from
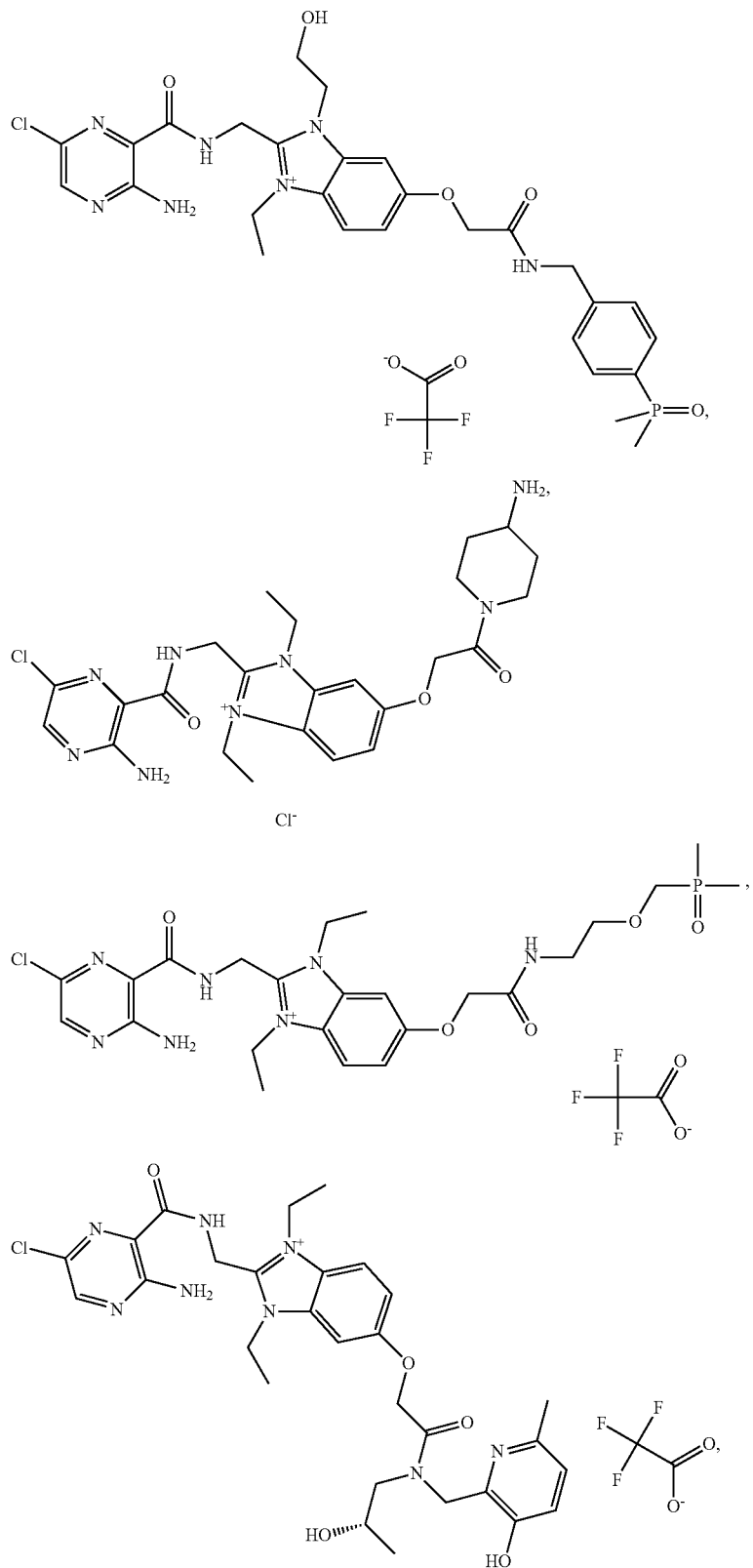

-continued
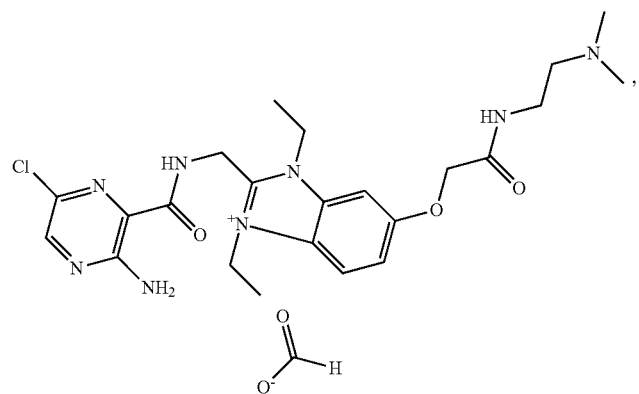
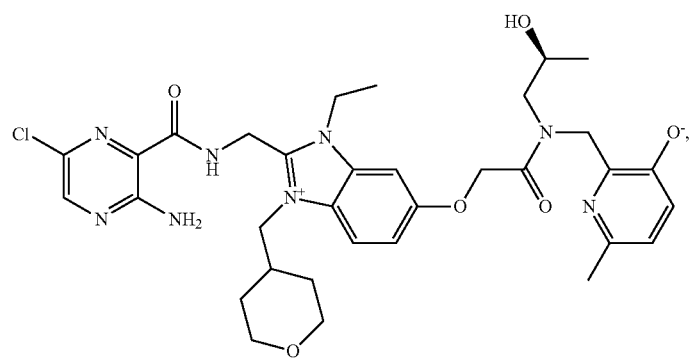
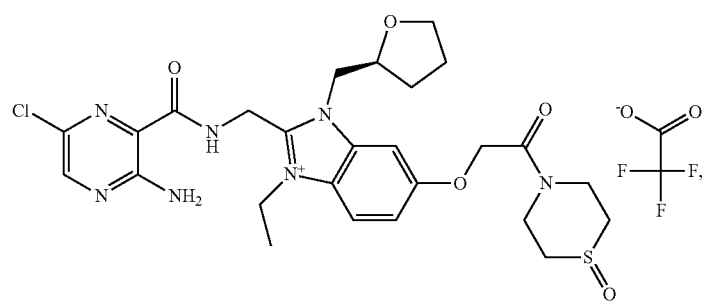
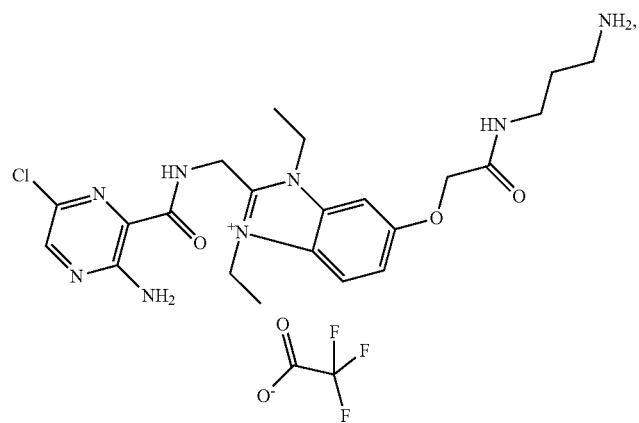

-continued

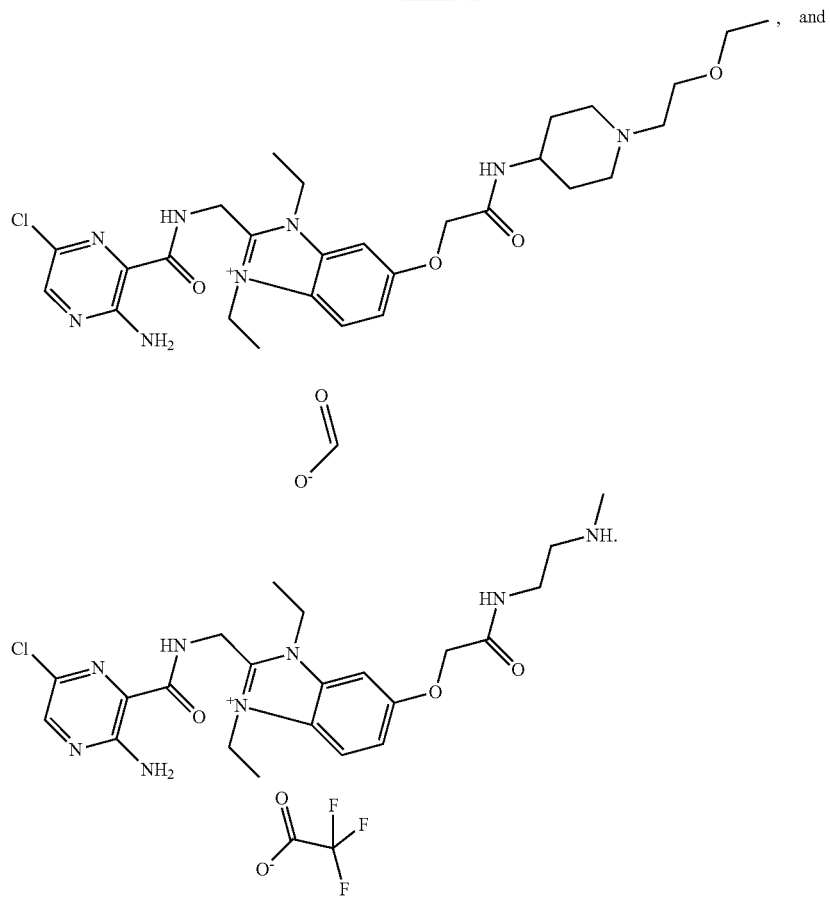

Another particular embodiment of the present invention relates to compounds of formula (I) characterized by a topological polar surface area value (TPSA) of at least 150. The term "topological polar surface area" as used herein refers to a value calculated as disclosed for the fragment based PSA in Ertl P. et al., J. Med. Chem, 43 (2000), 3714-3717. Such compounds of formula (I) will usually have a TPSA value in the range of from 150 to 250. Such compounds are in particular compounds selected from

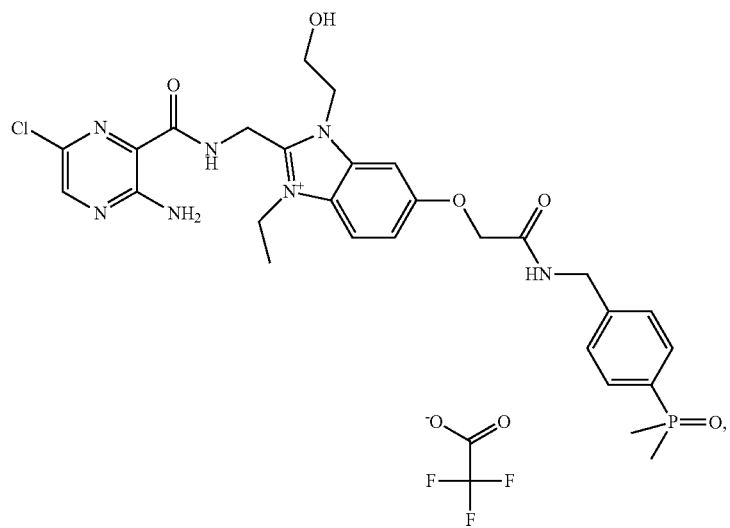

-continued
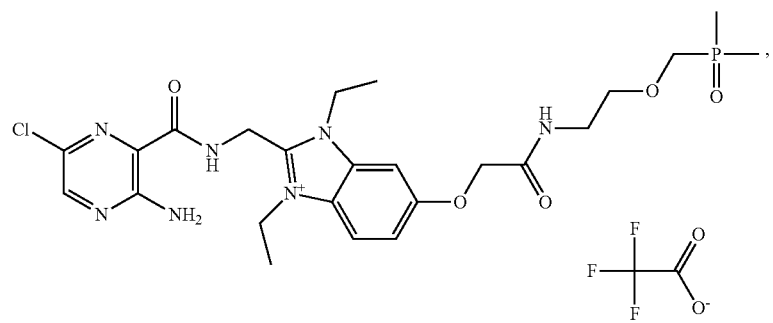
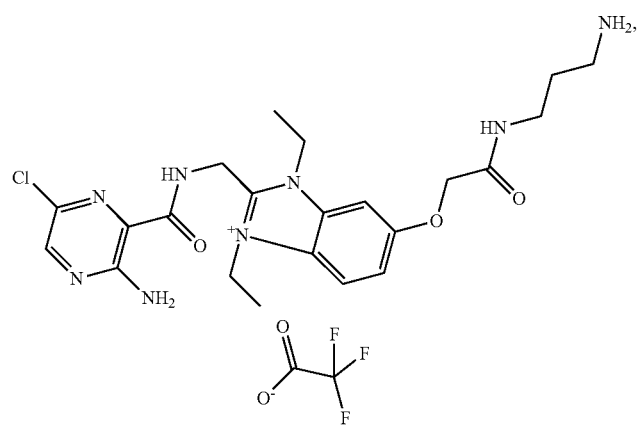
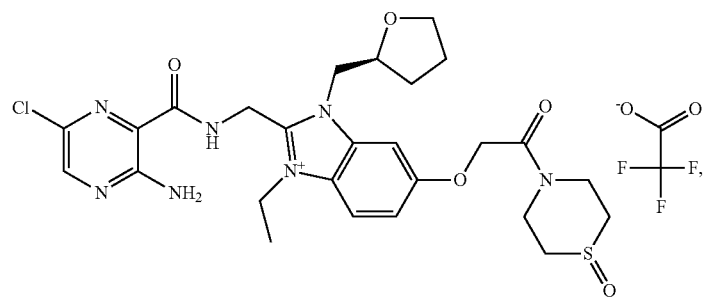
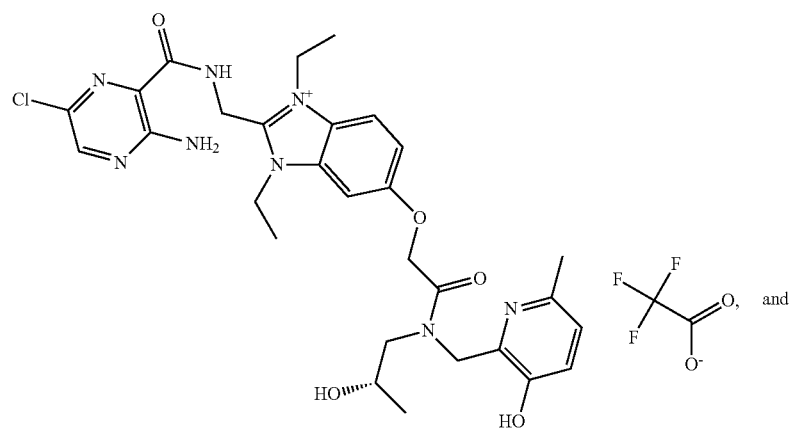

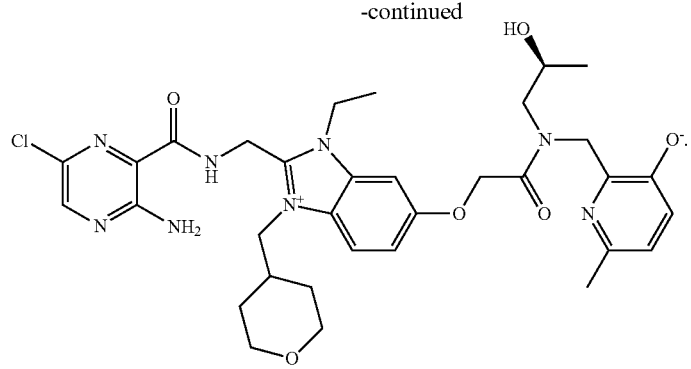

Any of the substituents defined above may be combined with each other to form additional compounds not specifically exemplified above. Particularly preferred are compounds of formula (I) or the pharmaceutically acceptable salts thereof wherein at least 2, 3, or 4 of the substituents defined herein have one of the particular or preferred meanings as defined herein.

Preparation

The following methods are suitable for preparing compounds of general formula (I).

The compounds according to the invention may be obtained using methods of synthesis which are known to the one skilled in the art and described in the literature of organic synthesis. General methods for functional groups protection and deprotection steps are described e.g. in: Greene, T. W. and Wuts, P. G. M. (eds.): Protective Groups in Organic Synthesis, third edition 1999; John Wiley and Sons, Inc. Preferably the compounds are obtained analogously to the methods of preparation explained more fully hereinafter, in particular as described in the experimental section.

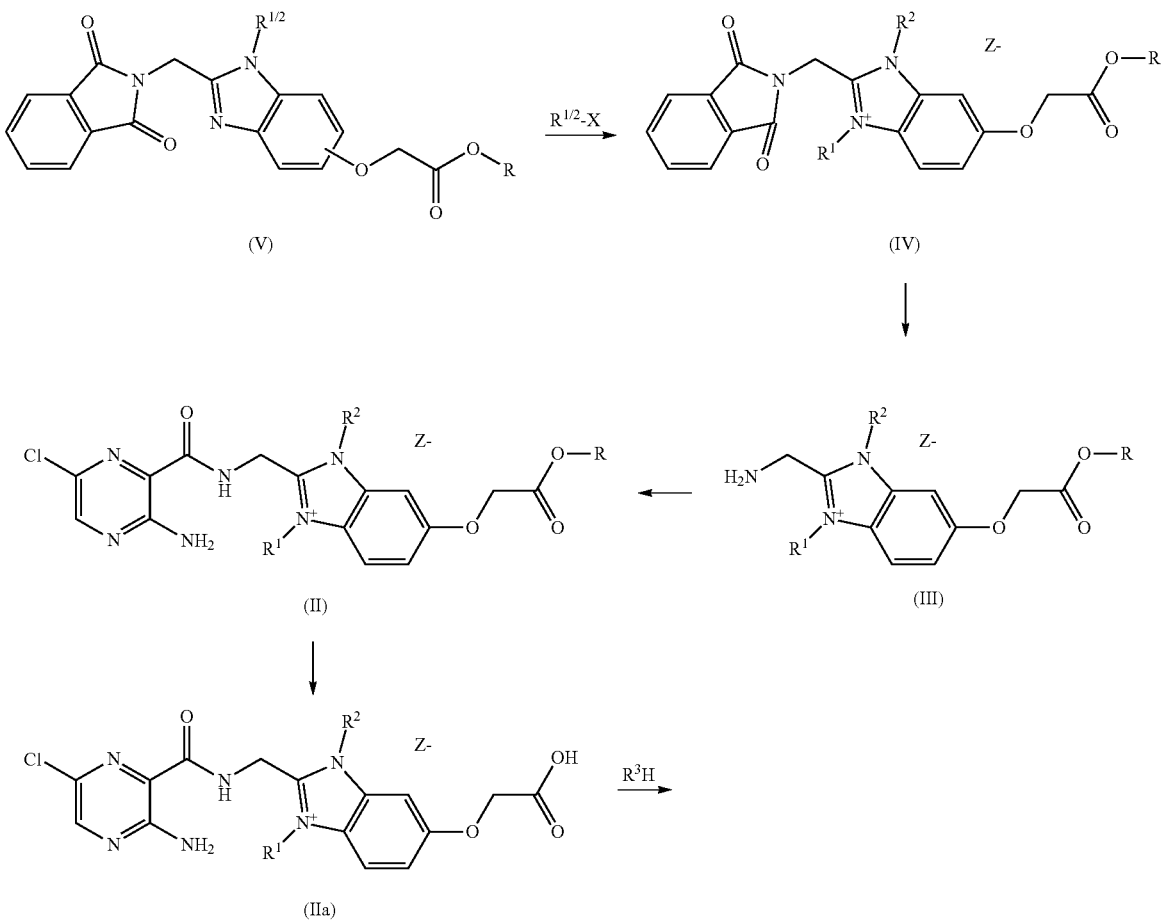

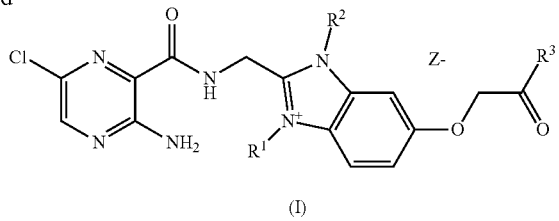

(I)

Compounds of general formula (I) can be prepared by standard amidation procedures from acids of general formula (IIa) and primary or secondary amines of general formula $R^3H$ applying e.g. the coupling reagent HATU. Obvious to the one skilled in the art, the counterion $Z^-$ of a permanently charged product, e.g. (I), may generally be different from the counterion $Z^-$ of the permanently charged starting material, e.g. (IIa), depending on the conditions of synthesis and purification. Amines $R^3H$ can be prepared using methods of synthesis which are known to one skilled in the art and described in the literature of organic synthesis. The scope of the substituents of amines $R^3H$ may exceed what is claimed for compounds of general formula (I) hereinafter. The substituents in compounds $R^3H$ may e.g. carry protecting groups necessary or advantageous in the amidation step. $R^3$ can be modified in subsequent synthetic steps through e.g. deprotection and/or amidation reactions.

Compounds of general formula (IIa) can be prepared by standard ester cleavage procedures from esters of general formula (II). The residue R in compounds of general formulas (II) through (XI) may be selected from e.g. methyl, ethyl, or tert-butyl. Furthermore, within the reaction sequence, the residue R may be changed by applying e.g. ester cleavage followed by esterification procedures.

Compounds of general formula (II) can be prepared by standard amidation procedures from amines of general formula (III) and 3-amino-6-chloro-pyrazine-2-carboxylic acid applying e.g. the coupling reagent HATU.

Amines of general formula (III) can be prepared from compounds of general formula (IV) by removing the phthalimide protecting group applying standard deprotection procedures, e.g. heating with hydrazine hydrate in ethanol.

Benzimidazolium compounds of general formula (IV) can be prepared by alkylation of benzimidazoles of general formula (V) by e.g. heating with an appropriate alkylating agent $R^1X$ or $R^2X$ (e.g. an optionally substituted alkyl bromide) in a suitable solvent like e.g. THF.

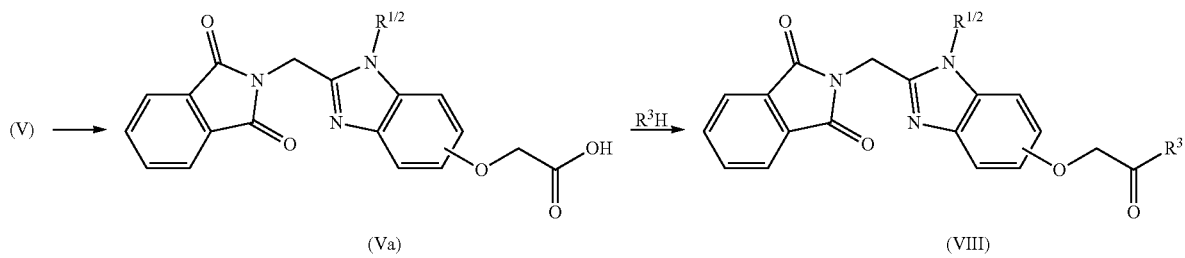

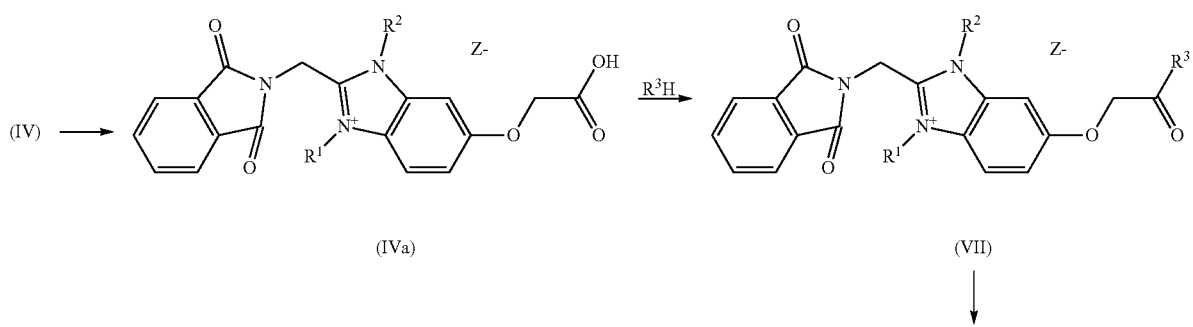

-continued

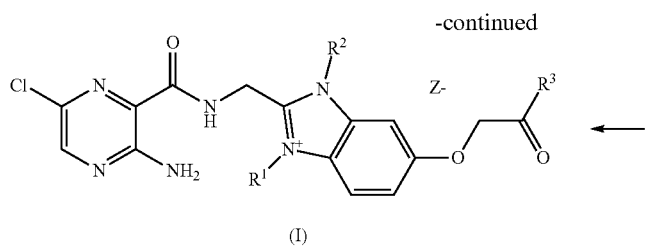

(I)

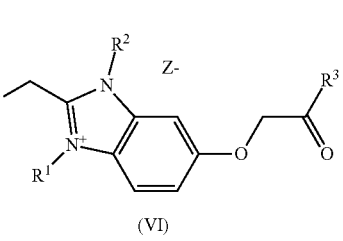

(VI)

Alternatively, compounds of general formula (I) can be prepared by standard amidation procedures from 3-amino-6-chloro-pyrazine-2-carboxylic acid and primary amines of general formula (VI) applying e.g. the coupling reagent HATU.

Amines of general formula (VI) can be prepared from compounds of general formula (VII) by removing the phthalimide protecting group applying standard deprotection procedures, e.g. heating with hydrazine hydrate in ethanol.

Compounds of general formula (VII) can be prepared by standard amidation procedures from acids of general formula (IVa) and primary or secondary amines of general formula $R^3H$ applying e.g. the coupling reagent HATU. Compounds of general formula (IVa) can be prepared by standard ester cleavage procedures from esters of general formula (IV). Alternatively, compounds of general formula (VII) can be prepared by alkylation of benzimidazoles of general formula (VIII) by e.g. heating with an appropriate alkylating agent $R^1X$ or $R^2X$ (e.g. an optionally substituted alkyl halide) in a suitable solvent like e.g. THF.

Compounds of general formula (VIII) can be prepared by standard amidation procedures from acids of general formula (Va) and primary or secondary amines of general formula $R^3H$ applying e.g. the coupling reagent HATU. Compounds of general formula (Va) can be prepared by standard ester cleavage procedures from esters of general formula (V).

Benzimidazoles of general formula (V) can be prepared from phenylenediamines (IX) in a two step procedure comprising (i) amidation with N-phthaloylglycine using e.g. the coupling reagent TBTU and (ii) ring closure under acid catalysis, e.g. in glacial acetic acid at elevated temperature. Phenylenediamines of general formula (IX) can be prepared from the respective nitroanilines (X) by standard nitro reduction conditions (e.g. catalytic hydrogenation using raney-nickel as a catalyst).

Nitroaninlines of general formula (X) can be prepared from aryl halides of general formula (XI) by nucleophilic substitution with a primary amine $H_2N-R^1$ or $H_2N-R^2$. The leaving group X in compounds (XI) may be F or Cl. The substituents $R^1$ or $R^2$ present in the amine applied may exceed the claims for $R^1$ and $R^2$ in compounds of general formula (I). $R^1$ and $R^2$ may e.g. contain protective groups that can be removed at later stages by standard deprotection procedures.

Aryl halides of general formula (XI) can be prepared by alkylation of appropriate nitro-halo-phenols (XII) with bromo- or chloroacetic acid esters at elevated temperature in the presence of a base like e.g. potassium carbonate in a solvent like e.g. ACN.

Compounds of formula (I), as defined hereinbefore, are salts containing an anion $Z^-$. These anions $Z^-$ may be derived from synthesis or purification or changed from one anionic species to another suitable anionic species by meth-

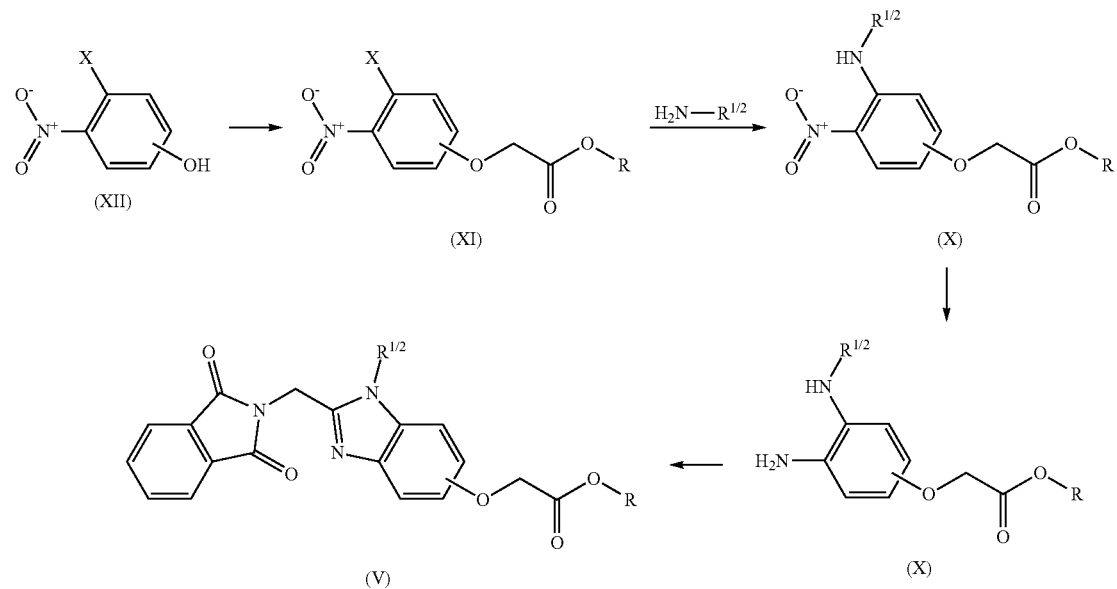

ods known to those skilled in the art. Examples of such methods are ion exchange using for example ion exchange resins or displacement of an acid counterion from its salt using another, usually stronger, acid. For example, treatment of a compound of formula (I), as defined hereinbefore, where $Z^-$ is $CF_3COO^-$, with HCl in a suitable solvent, such as water, methanol or diethyl ether, may produce a compound of formula 1, as defined hereinbefore, where $Z^-$ is $Cl^-$.

Certain compounds of formula (I), as defined hereinbefore, may contain groups that may be further converted into the salts thereof, for pharmaceutical use particularly into pharmaceutically acceptable salts with inorganic or organic acids and bases. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known to the skilled person.

Moreover, where one or more stereoisomers may exist, the compounds of general formula (I) or intermediates in the synthesis of compounds of general formula (I) may be obtained as mixtures and then resolved into their stereoisomers, e.g. enantiomers and/or diastereomers. Thus, for example, cis/trans mixtures may be resolved into their cis and trans isomers, and racemic compounds may be separated into their enantiomers.

Thus, for example, the cis/trans mixtures may be resolved by chromatography into the cis and trans isomers thereof. The compounds of general formula (I) or intermediates in the synthesis of compounds of general formula (I), which occur as racemates may be separated by methods known per se (cf. Allinger N. L. and Eliel E. L. in "Topics in Stereochemistry", Vol. 6, Wiley Interscience, 1971) into their optical antipodes and compounds of general formula (I) or intermediates in the synthesis of compounds of general formula (I) with at least 2 asymmetric carbon atoms may be resolved into their diastereomers on the basis of their physical-chemical differences using methods known per se, e.g. by chromatography and/or fractional crystallization, and, if these compounds are obtained in racemic form, they may subsequently be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoluoyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

EXAMPLES

Other features and advantages of the present invention will become apparent from the following more detailed examples which illustrate, by way of example, the principles of the invention.

Where no salt forms of compounds are specified, the compound may exist as a free base or a salt or a zwitterion, depending on the chemical structure, the synthesis conditions and the processes of workup and purification applied. The skilled person will appreciate that the compound is not limited to a certain salt form. Where salt forms of compounds are specified, the stoichiometry of the counterion is usually omitted. In case of multiply charged counterions the skilled person will appreciate that the resulting salt form is uncharged, leading to the corresponding stoichiometry. The skilled person will appreciate that the compound is not limited to the mono salt form and that it may exist as a disalt, trisalt or other compound: counterion stoichiometries. Furthermore, the skilled person will appreciate that such compound may unexpectedly exist as a salt with a different counterion, depending on the synthesis conditions and the processes of workup and purification applied. Solely for the purpose of yield determination, an estimate of the nature of the counterion and of compound: counterion stoichiometry is made (as indicated by the formula given).

SYNTHESIS OF INTERMEDIATES

The following intermediates can be prepared as described in the literature given in the table:

| Intermediate No. | Structure | Literature and comments |
|---|---|---|
| I.1 | [3-fluoro-4-nitrophenoxyacetic acid ethyl ester] | US2015/18315 ("compound VII.2") |
| I.2 | [3-fluoro-4-nitrophenoxyacetic acid tert-butyl ester] | US2009/163552 |
| I.3 | [4-fluoro-3-nitrophenoxyacetic acid tert-butyl ester] | Intermediate I.3 can be prepared starting from 4-fluoro-3-nitrophenol analogously to the procedure described for the synthesis of intermediate I.2 (US2009/163552). |
| I.4 | $H_2N\text{-}CH_2CH_2\text{-}O\text{-}CH_2\text{-}P(=O)(CH_3)_2$ | Zeitschrift fuer Naturforschung, B: Chemical Sciences 50, 7 (1995) 1086-90 |
| I.5 | [(S)-1-((3-hydroxy-6-methylpyridin-2-yl)methylamino)propan-2-ol] | Intermediate I.5 can be prepared analogously to the procedure described for the synthesis of 6-Methyl-2-(methylaminomethyl)-pyridin-3-ol in J. Am. Chem. Soc. 71 (1949) 2968-71. |

Intermediate II.1

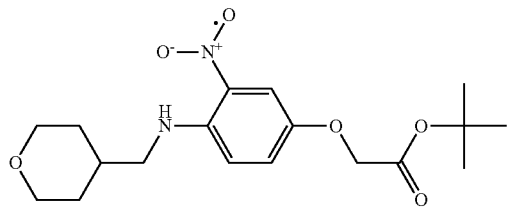

I.1

A mixture of the aryl halide intermediate 1.3 (17.2 g; 63.6 mmol), (tetrahydropyran-4-yl)methylamine (11.5 g; 99.6 mmol) and potassium carbonate (13.2 g; 95.3 mmol) in ACN (100 ml) is stirred at 60° C. for 2 h. The mixture is evaporated and the residue is taken up in EE and washed with brine. The organic layer is separated, dried (MgSO$_4$) and evaporated.

$C_{18}H_{26}N_2O_6$ ESI Mass spectrum: m/z=367 [M+H]+

The following intermediates are prepared accordingly from the respective aryl halide and the respective amine as indicated. Depending on conditions applied, the syntheses may yield a free base, a TFA salt or other salt forms which can be applied equally to the syntheses of example compounds described below.

| Intermediate No. | Structure | Aryl halide applied | amine applied | Synthesis comment |
|---|---|---|---|---|
| II.2 | [2-((2-hydroxyethyl)amino)-4-(2-ethoxy-2-oxoethoxy)nitrobenzene] | I.1 | HOCH$_2$CH$_2$NH$_2$ | 2 eq. amine; no additional base; solvent: methyl-THF |

-continued

| Intermediate No. | Structure | Aryl halide applied | amine applied | Synthesis comment |
|---|---|---|---|---|
| II.3 | 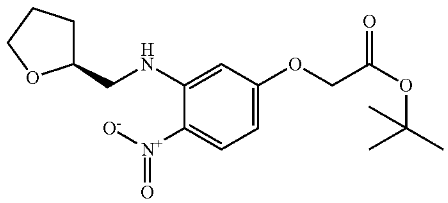 [SMILES: CC(C)(C)OC(=O)COc1ccc([N+](=O)[O-])c(NC[C@@H]2CCCO2)c1] | I.2 | | 2 eq. amine; no additional base; solvent: THF; reaction at r.t. |
| II.4 | 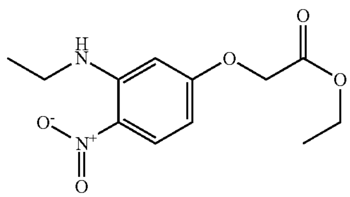 [SMILES: CCNc1cc(OCC(=O)OCC)ccc1[N+](=O)[O-]] | I.3 | | 2 eq. amine; no additional base; solvent: THF; reaction at r.t. |

Intermediate III.1

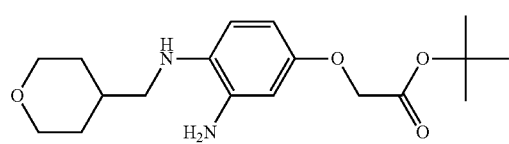

III.1

Intermediate II.1 (23.1 g; 63.1 mmol) in THF (200 ml) is hydrogenated in a Parr apparatus (50° C.; 3 bar hydrogen; catalyst: 2.00 g Raney-Nickel. The catalyst is filtered off and the solvent is evaporated.

$C_{18}H_{28}N_2O_4$

HPLC analytics: RT=0.45 min (HPLC method A)

The following intermediates are prepared accordingly from the respective starting material as indicated. Depending on conditions applied, the syntheses may yield a free base, a TFA salt or other salt forms which can be applied equally to the syntheses of example compounds described below.

| Intermediate No. | Structure | Starting material applied | Synthesis comment |
|---|---|---|---|
| III.2 | 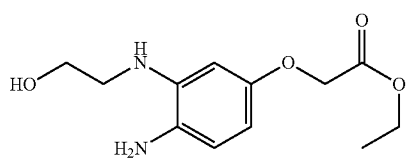 [SMILES: CCOC(=O)COc1ccc(N)c(NCCO)c1] | II.2 | |
| III.3 | 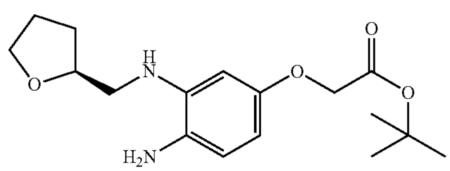 [SMILES: CC(C)(C)OC(=O)COc1ccc(N)c(NC[C@@H]2CCCO2)c1] | II.3 | Reaction at r.t.; catalyst: PD/C 5% |
| III.4 | 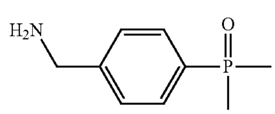 | VII.1 | Reaction in methanolic ammonia at r.t. |
| III.5 | 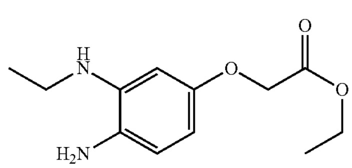 [SMILES: CCNc1cc(OCC(=O)OCC)ccc1N] | II.4 | catalyst: Pd/C 5% |

Intermediate IV.1

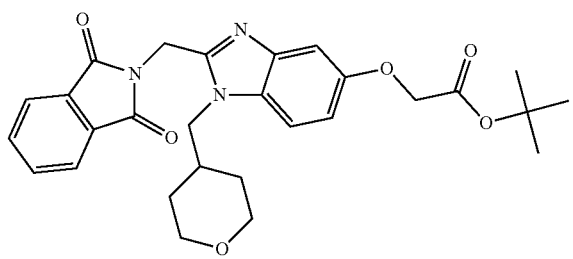

layer is separated and evaporated. The residue is triturated with TBDME, filtered off with suction and dried at 50° C.

$C_{28}H_{31}N_3O_6$ ESI Mass spectrum: m/z=506 [M+H]+

The following intermediates are prepared accordingly from the respective diamino compound as indicated. In cases where precipitation does not occur, the intermediates are extracted. Depending on conditions applied, the syntheses may yield a free base, a TFA salt or other salt forms which can be applied equally to the syntheses of example compounds described below.

| Intermediate No. | Structure | diamino compound applied | Synthesis comment |
|---|---|---|---|
| IV.2 | 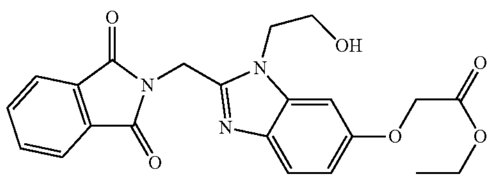 [SMILES: CCOC(=O)COc1ccc2nc(CN3C(=O)c4ccccc4C3=O)n(CCO)c2c1] | III.2 | Crystallization from EE |
| IV.3 | 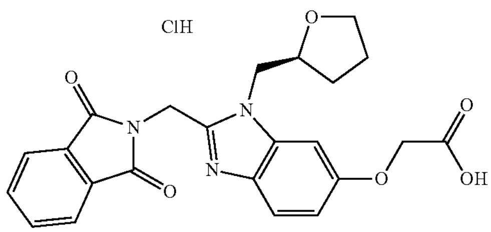 [SMILES: O=C(O)COc1ccc2nc(CN3C(=O)c4ccccc4C3=O)n(C[C@@H]3CCCO3)c2c1 ; Cl] | III.3 | Step 2: reaction in AcOH at 100° C.; crude product stirred in HCl (4 M in dioxane) at 100° C. for 4 h, evaporated, triturated with diethyl ether |
| IV.4 | 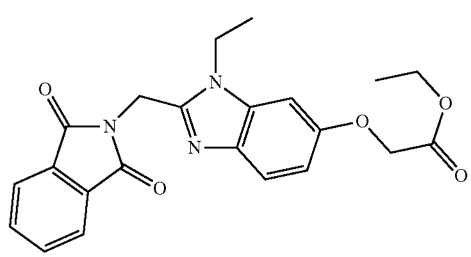 [SMILES: CCOC(=O)COc1ccc2nc(CN3C(=O)c4ccccc4C3=O)n(CC)c2c1] | III.5 | Crystallized from ACN |

Step 1:

A mixture of the diamino intermediate III.1 (21.2 g; 63.1 mmol), THF (250 ml), N-phthaloyl glycine (13.0 g; 63.1 mmol), TBTU (20.3 g; 63.14 mmol) and triethylamine (9.63 ml; 69.4 mmol) is stirred at RT for 4 h. The mixture is poured on ice-water (800 ml) and stirred until the ice is melted. The precipitate is filtered off with suction, washed with water and dried at 65° C.

Step 2:

The so formed intermediate is taken up in acetic acid (30 ml) and dioxane (120 ml) and stirred at 95° C. overnight. The mixture is evaporated, taken up in EE and extracted successively with $Na_2CO_3$ solution and water. The organic Intermediate V.1

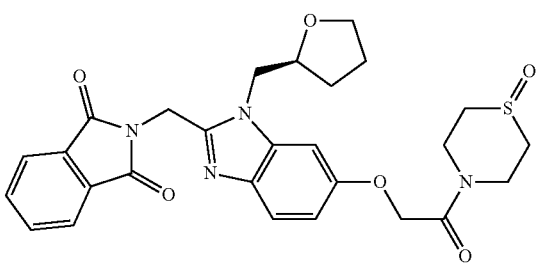

A mixture of the acid intermediate IV.3 (2.00 g; 4.24 mmol), the amine thiomorpholine-1-oxide (505 mg; 4.24 mmol), TBTU (1.36 g; 4.24 mmol), triethylamine (1.19 ml; 8.48 mmol) and DMF (20 ml) is stirred at r.t. for 2 h. The mixture is poured on ice-water, then extracted with EE. The organic layer is separated, dried (MgSO$_4$), filtered and evaporated. The residue is purified by silica gel chromatography (DCM/MeOH 0→10%).

C$_{27}$H$_{28}$N$_4$O$_6$S ESI Mass spectrum: m/z=537 [M+H]+

The following compounds are prepared accordingly applying the respective acid and amine as indicated. Depending on conditions applied, the procedures may yield a chloride salt, a TFA salt or bis-TFA salt, a zwitterion or other salt forms.

Step 1:

A mixture of the benzimidazole intermediate IV.2 (5.00 g; 11.8 mmol), iodoethane (4.77 ml; 59.0 mmol) and ACN 50 ml) is heated to 120° C. (microwave irradiation; closed vessel) for 2 h.

Step 2:

The mixture is evaporated and the residue is stirred at 65° C. for 1 h in aq. HCl (4 mol/l; 50 ml; 200 mmol). The mixture is freeze-dried.

| Intermediate No. | Structure | Acid applied | Amine applied | Synthesis comment |
|---|---|---|---|---|
| V.2 | 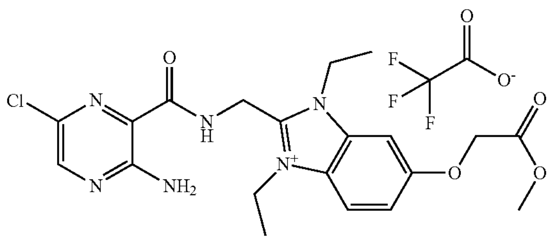 [SMILES: CCn1c(CNC(=O)c2nc(Cl)cnc2N)[n+](CC)c2ccc(OCC(=O)OC)cc21 ; O=C([O-])C(F)(F)F] | | XI.1 | Purification by RP-HPLC (C18; water-ACN-TFA) |

Intermediate VI.1

VI.1

Workup: The residue is purified by RP-HPLC (C18; water/ACN/TFA).

C$_{22}$H$_{22}$N$_3$O$_6$ ESI Mass spectrum: m/z=424 [M+H]+

HPLC analytics: RT=0.37 min (HPLC method A)

The following intermediates are prepared accordingly from the respective benzimidazole as indicated. Depending on conditions applied, the syntheses may yield a free base, a TFA salt or other salt forms which can be applied equally to the syntheses of example compounds described below.

| Intermediate No. | Structure | Benzimidazole applied | Synthesis comment |
|---|---|---|---|
| VI.2 | 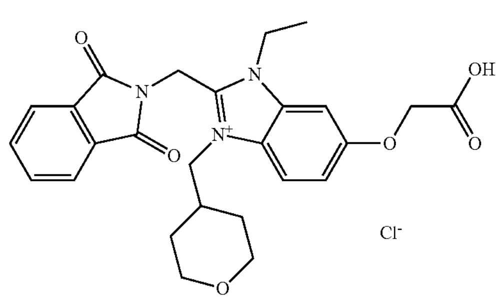 [SMILES: CCn1c(CN2C(=O)c3ccccc3C2=O)[n+](CC2CCOCC2)c2ccc(OCC(=O)O)cc21 ; [Cl-]] | IV.1 | Step 2: reaction at 80° C.; product filtered off upon cooling to r.t.; no freeze-drying nor chromatography |

| Intermediate No. | Structure | Benzimidazole applied | Synthesis comment |
|---|---|---|---|
| VI.3 | 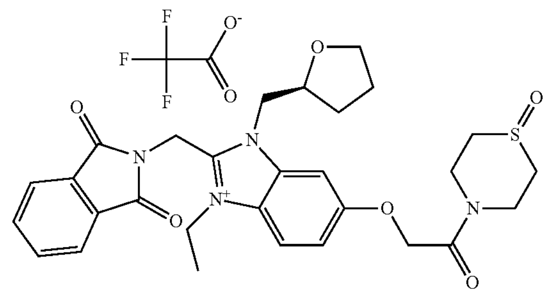 [SMILES: CC[n+]1c(CN2C(=O)c3ccccc3C2=O)n(C[C@@H]2CCCO2)c2cc(OCC(=O)N3CCS(=O)CC3)ccc21 ; O=C([O-])C(F)(F)F] | V.1 | Step 2 omitted |
| VI.4 | 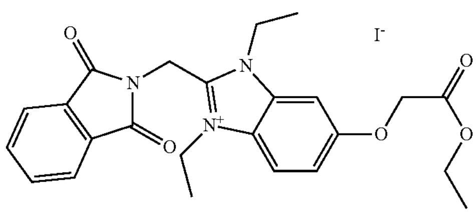 [SMILES: CCOC(=O)COc1ccc2c(c1)n(CC)c(CN1C(=O)c3ccccc3C1=O)[n+]2CC ; [I-]] | IV.4 | Step 2 omitted |

Intermediate VII.1

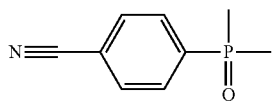

VII.1

A mixture of 4-iodobenzonitrile (2.29 g; 10.0 mmol), dimethylphosphinoxide (800 mg; 10.3 mmol), triethylamine (6.97 ml; 50 mmol) and ACN (50 ml) is degassed and kept under Argon atmosphere. Xantphos (400 mg; 0.691 mmol), tris(dibenzylideneacetone)dipalladium (300 mg; 0.328 mmol) and cesium carbonate (4.0 g; 12.3 mmol) are added and the mixture is stirred under Argon at 80° C. for 2 h. Water is added and the mixture is extracted with EE. The organic layer is separated, dried (MgSO$_4$) and evaporated. The residue is purified by silica gel chromatography (DCM/MeOH 0→15%).

$C_9H_{10}NOP$

HPLC analytics: RT=0.59 min (HPLC method B)

Intermediate VIII.1

Step 1:
The acid intermediate VI.1 (1.06 g; 1.97 mmol) is taken up in THF (10 ml).

Step 2:
TBDMS chloride (594 mg; 3.94 mmol) and imidazole (268 mg; 3.94 mmol) are added and the mixture is stirred at r.t. for 3 days.

Step 3:
CDI (479 mg; 2.96 mmol) is added, and after 30 min stirring, the amine intermediate III.4 (360 mg; 1.97 mmol) is added and the mixture is further stirred overnight.

Step 4:
TFA (3 ml) is added and the mixture is stirred at r.t for 1 h.

Workup: The mixture is evaporated and the residue is purified by RP-HPLC (C18; water/ACN/TFA).

$C_{31}H_{34}N_4O_6P$ ESI Mass spectrum: m/z=589 [M+H]+

HPLC analytics: RT=0.39 min (HPLC method A)

The following compounds are prepared accordingly applying the respective acid and amine as indicated. Depending on conditions applied, the procedures may yield a chloride salt, a TFA salt or bis-TFA salt, a zwitterion or other salt forms.

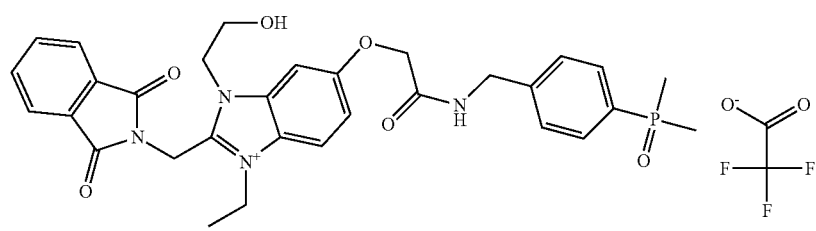

VIII.1

| Intermediate No. | Structure | Acid applied | Amine applied | Synthesis comment |
|---|---|---|---|---|
| VIII.2 | 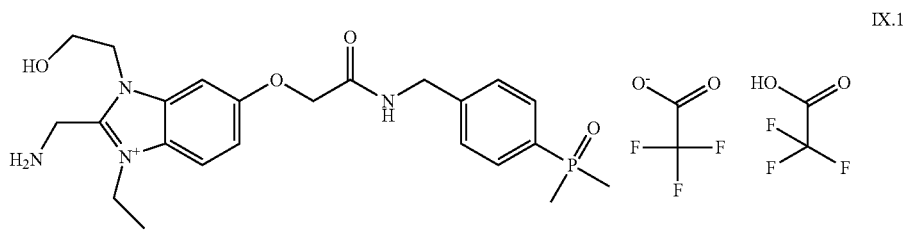 [SMILES: CC[n+]1c(CN)n(CCO)c2cc(OCC(=O)NCc3ccc(P(C)(C)=O)cc3)ccc21 ; O=C([O-])C(F)(F)F ; O=C(O)C(F)(F)F] | VI.2 | I.5 | Steps 2 and 4 omitted |

Intermediate IX.1

IX.1

A mixture of intermediate VIII.1 (210 mg; 0.254 mmol), hydrazine hydrate (57.8 µl; 0.762 mmol) and ethanol (5 ml) is stirred at 70° C. (bath temperature) for 2 h. Insolubles are filtered off by suction, the filtrate is evaporated and purified by RP-HPLC (C18, water/ACN/TFA).
$C_{23}H_{32}N_4O_4P \times C_2O_2F_3 \times C_2HO_2F_3$ ESI Mass spectrum: m/z=459 [M+H]+

HPLC analytics: RT=0.26 min (HPLC method A)

The following intermediates are prepared accordingly from the respective protected amines as indicated. Depending on conditions applied, the syntheses may yield a TFA salt or other salt forms which can be applied equally to further synthesis steps.

| Intermediate | Structure | Protected amine applied | Synthesis comment |
|---|---|---|---|
| IX.2 | 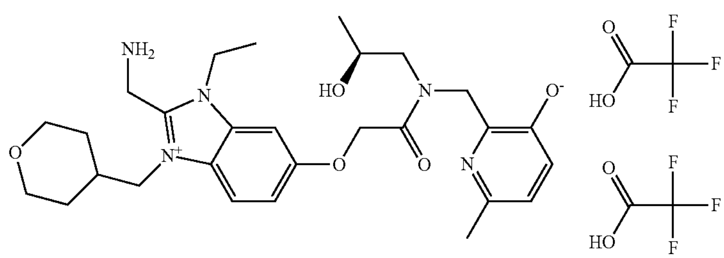 | CIII.2 | |
| IX.3 | 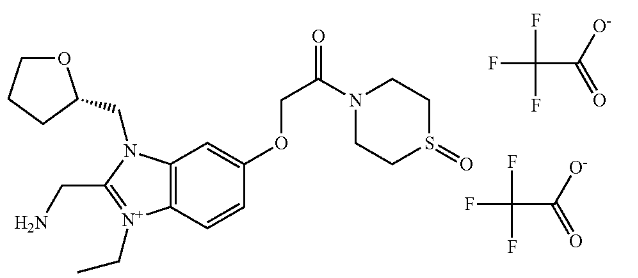 [SMILES: CC[n+]1c(CN)n(C[C@@H]2CCCO2)c2cc(OCC(=O)N3CCS(=O)CC3)ccc21 ; O=C([O-])C(F)(F)F ; O=C([O-])C(F)(F)F] | CI.3 | |

| Intermediate | Structure | Protected amine applied | Synthesis comment |
|---|---|---|---|
| IX.4 | 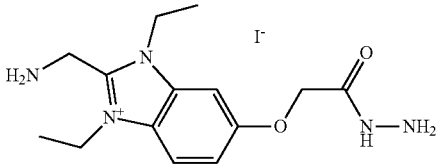 [SMILES: CCn1c(CN)[n+](CC)c2ccc(OCC(=O)NN)cc21 ; [I-]] | VI.4 | Reaction in ACN/EtOH 1:1; 5 eq. hydrazine hydrate |

Intermediate X.1

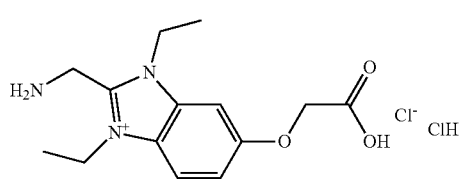

X.1

A mixture of intermediate IX.4 (13.5 g; 32.2 mmol) and aq. HCl (4 mol/l; 100 ml; 400 mmol) is stirred at 80° C. for 2 h, then cooled to r.t. Insolubles are filtered off and discarded. The filtrate is freeze-dried after addition of ACN.
$C_{14}H_{20}N_3O_3 \times HCl \times Cl$ ESI Mass spectrum: m/z=278 [M]+

Intermediate XI.1

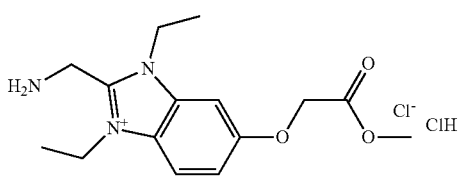

XI.1

A mixture of intermediate X.1 (14.3 g; 40.8 mmol) and methanolic HCl (50 ml) is refluxed for 30 min, then filtered hot and evaporated to dryness.
$C_{15}H_{22}N_3O_3 \times HCl \times Cl$ ESI Mass spectrum: m/z=292 [M]+

Intermediate XII.1

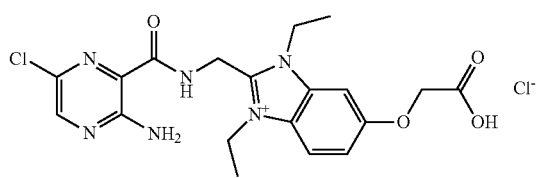

XII.1

A mixture of intermediate V.2 (2.00 g; 3.57 mmol) and aq. HCl (1 mol/l; 7.13 ml; 7.13 mmol) is stirred at 50° C. overnight. The mixture is cooled to 1° C., the precipitate formed is filtered off with suction and dried at 50° C.
$C_{19}H_{22}ClN_6O_4 \times Cl$ ESI Mass spectrum: m/z=433 [M]+

Intermediate XIII.1

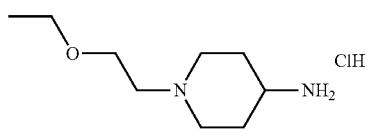

XIII.1

Step 1:
To a mixture of 4-(BOC-amino)-piperidine (1.00 g; 4.99 mmol), DIPEA (1.72 ml; 9.99 mmol) and DMF (3.0 ml) is added dropwise at r.t. 2-bromoethyl-ethylether (840 mg; 5.49 mmol). The mixture is stirred for further 2 h, then water is added and the mixture is extracted with diethyl ether. The organic layer is separated, dried and evaporated to dryness.

Step 2:
The BOC-protected intermediate obtained from step 1 is suspended in aq. HCl (6.10 ml; 24.4 mmol). The mixture is stirred at r.t. for 1 h, then evaporated to dryness.
$C_9H_{20}N_2O \times HCl$

SYNTHESIS OF EXAMPLES

Example 1.01

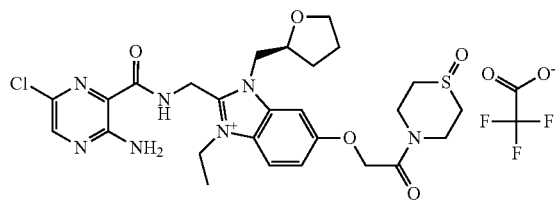

1.1

A mixture of 3-amino-6-chloro-pyrazine-2-carboxylic acid (26.0 mg; 0.150 mmol), the amine intermediate IX.3 (100 mg; 0.151 mmol), TBTU (53.0 mg; 0.165 mmol), triethylamine (63.2 µl; 0.450 mmol) and DMF (5.0 ml) is stirred at r.t. overnight. Volatiles are evaporated and the residue is purified by RP-HPLC (C18; water-ACN-TFA).
$C_{26}H_{33}ClN_7O_5S \times C_2O_2F_3$ ESI Mass spectrum: m/z=590 [M+H]+
HPLC analytics: RT=0.42 min (HPLC method D)
The following example compounds are prepared accordingly from the respective amine as indicated. Depending on conditions applied, the syntheses may unexpectedly yield other counterion stoichiometries or other salt forms.

| Example No. | Structure | Amine applied | M+ | RT (min) | HPLC method |
|---|---|---|---|---|---|
| 1.02 | 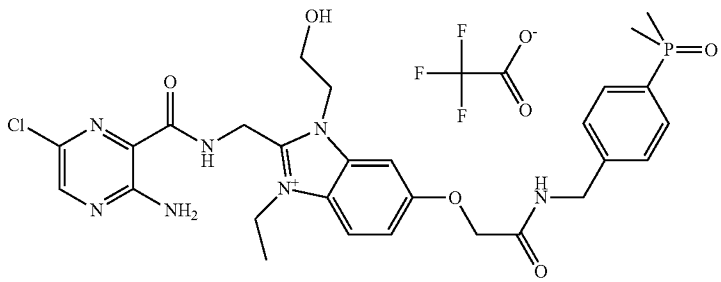 [SMILES: CC[n+]1c(CNC(=O)c2nc(Cl)cnc2N)n(CCO)c2cc(OCC(=O)NCc3ccc(P(C)(C)=O)cc3)ccc21 ; O=C([O-])C(F)(F)F] | IX.1 | 614 | 0.39 | A |
| 1.03 | 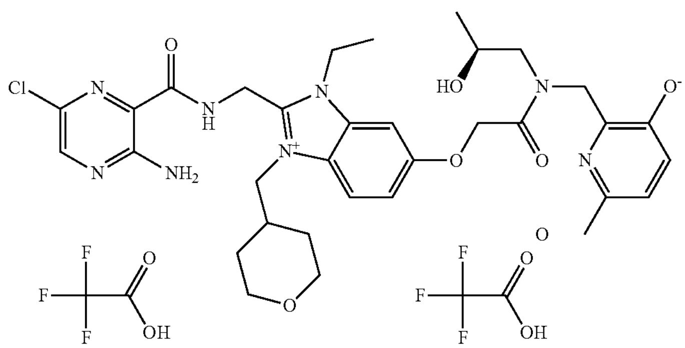 | IX.2 | 681 (M + H)+ | 0.38 | A |

Example 2.01

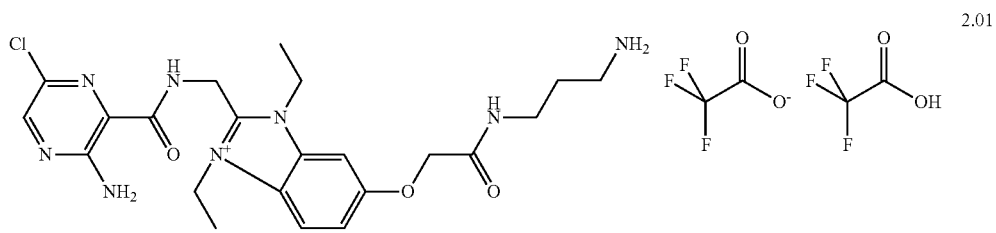 [SMILES: CCn1c(CNC(=O)c2nc(Cl)cnc2N)[n+](CC)c2ccc(OCC(=O)NCCCN)cc21 ; O=C([O-])C(F)(F)F ; O=C(O)C(F)(F)F]

Step 1:
To a mixture of intermediate XII.1 (120 mg; 0.243 mmol), TBTU (156 mg; 0.486 mmol), triethylamine (101 µl; 0.729 mmol) and DMF (3.0 ml) is added the amine tert-butyl N-(3-aminopropyl)carbamate (42.3 mg; 0.243 mmol). The mixture is stirred at r.t. for 3 h, then evaporated.

Step 2:
The BOC-protected intermediate is purified by RP-HPLC (C18; water-ACN-TFA), taken up in aq. HCl (37%; 1.0 ml) and evaporated to dryness.

Step 3:
The crude product is purified by RP-HPLC (C18; water-ACN-TFA).

$C_{22}H_{30}ClN_8O_3 \times C_2O_2F_3 \times C_2HO_2F_3$ ESI Mass spectrum: m/z=489 [M+H]+

HPLC analytics: RT=3.02 min (HPLC method C)

The following example compounds are prepared accordingly from the respective amine as indicated. Depending on conditions applied, the syntheses may unexpectedly yield other counterion stoichiometries or other salt forms.

| Example No. | Structure | Amine applied | Synthesis comment | M+ | RT (min) | HPLC method |
|---|---|---|---|---|---|---|
| 2.02 | 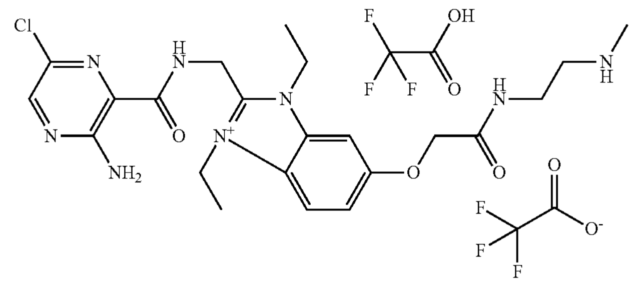 [SMILES: CCn1c(CNC(=O)c2nc(Cl)cnc2N)[n+](CC)c2ccc(OCC(=O)NCCNC)cc21 ; O=C(O)C(F)(F)F ; O=C([O-])C(F)(F)F] | | | 489 | 2.97 | C |
| 2.03 | 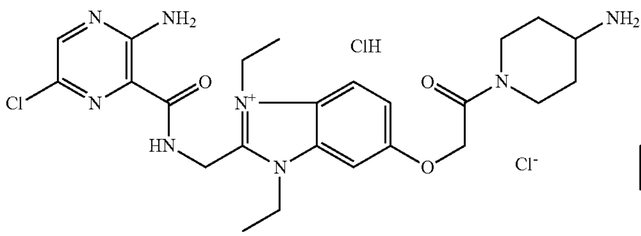 [SMILES: CCn1c(CNC(=O)c2nc(Cl)cnc2N)[n+](CC)c2ccc(OCC(=O)N3CCC(N)CC3)cc21 ; Cl ; [Cl-]] | | Step 3 omitted | 515 | 3.05 | C |
| 2.04 | 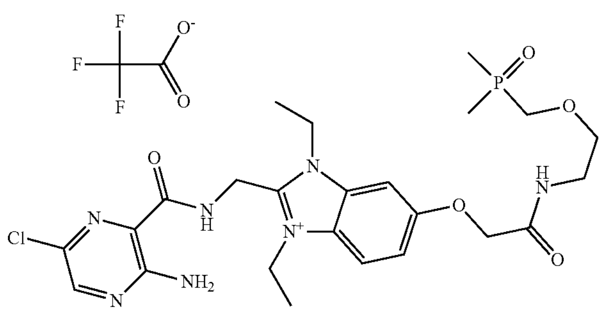 [SMILES: CCn1c(CNC(=O)c2nc(Cl)cnc2N)[n+](CC)c2ccc(OCC(=O)NCCOCP(C)(C)=O)cc21 ; O=C([O-])C(F)(F)F] | 1.4 | Step 2 omitted | 566 | 0.38 | A |
| 2.05 | 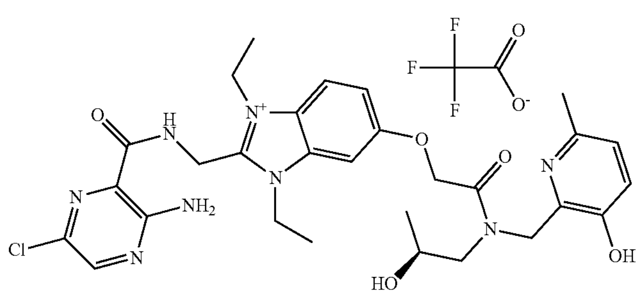 [SMILES: CCn1c(CNC(=O)c2nc(Cl)cnc2N)[n+](CC)c2ccc(OCC(=O)N(Cc3nc(C)ccc3O)C[C@H](C)O)cc21 ; O=C([O-])C(F)(F)F] | 1.5 | Step 2 omitted | 611 | 0.37 | A |
| 2.06 | 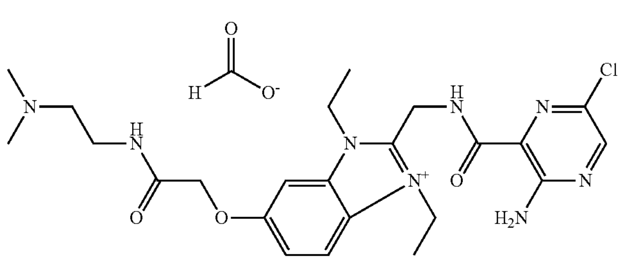 | | Footnote (a) | 503 | 3.03 | C |

| Example No. | Structure | Amine applied | Synthesis comment | M+ | RT (min) | HPLC method |
|---|---|---|---|---|---|---|
| 2.07 | (structure) | XIII.1 | Footnote (a) | 587 | 3.28 | C |

(a) Step 2 omitted; purification by RP-HPLC (C18; water-ACN-formic acid)

(a) Step 2 omitted; purification by RP-HPLC (C18; water-ACN-formic acid)

Analytical Methods and Preparative Chromatography

As a rule, 1H-NMR and mass spectra have been obtained for the compounds prepared. Mass peaks given (e.g. (M)+, (M+H)+, (M+HCOO)—) refer to monoisotopic molecular weight.

Preparative HPLC:

Stationary phase (unless stated otherwise): XBridge C18; 10 μm or SunFire C18; 10 μm (both from waters, www.waters.com)

Analytical HPLC/MS Methods

The HPLC retention times given are measured under the following parameters.

HPLC Method A

| Column: | | SunFire C18, 2.1 × 30 mm, 2.5 μm (Waters) | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

HPLC Method B

| Column: | | SunFire, 3 × 30 mm, 2.5 μm (Waters) | | |
|---|---|---|---|---|
| Gradient time [min] | % Sol [H2O, 0.1% TFA] | % Sol [ACN] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

HPLC Method C

Column: Atlantis dC18 5 μm 4.6×50 mm, Temp 35° C.

Mobile phase: A=H2O 90%+10% CH3CN+CF3COOH 0.05%

B=CH3CN 90%+10% H2O

| Time in min | % A | % B | flow rate in ml/min |
|---|---|---|---|
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

HPLC Method D

| Column: | | XBridge BEH C18, 2.1 × 30 mm, 1.7 μm (Waters) | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

The following abbreviations are used above and hereinafter:
ACN Acetonitrile
Aq. Aqueous
BOC tert-Butoxycarbonyl
Cbz Carbobenzyloxy
CH Cyclohexane
DCM Dichloromethane
DIPEA Diisopropyl-ethylamine
DMAP 4-Dimethylaminopyridine
DMF N,N-Dimethylformamide
DPPF 1,1'-Bis(diphenylphosphino)ferrocene
EDC 1-Ethyl-3-(3-dimethylaminopropyl)carbodiimide hydrochloride
EE Ethyl acetate
Eq. Molar equivalent
ESI Electrospray ionization
h Hour
HATU O-(7-Azabenzotriazol-1-yl)-N,N,N',N'-tetramethyluronium hexafluorophosphate
HCl Hydrochloric acid
KOH Potassium hydroxide
l Liter
LiHMDS Lithium bis(trimethylsilyl)amide
M mol/l
Min Minutes
Mp melting point
NaOH Sodium hydroxide n.d. not determined
NMP N-Methylpyrrolidone
Pd/C palladium on charcoal
r.t. ambient temperature (about 20° C.)
RT retention time
TBME Methyl tert-butyl ether
TBDMS Tert-butyl-dimethylsilyl
TBTU 2-(1H-Benzotriazol-1-yl)-1,1,3,3-tetramethyluronium-tetrafluoroborate
TEA Triethylamine
TFA Trifluoroacetic acid
THF Tetrahydrofurane
TLC Thin Layer Chromatography
TMS Trimethylsilyl
Xantphos 4,5-Bis(diphenylphosphino)-9,9-dimethylxanthene Pharmacological Test Method The $IC_{50}$ values of the example compounds given above were determined in the Ussing Chamber assay.

Ussing Chamber: Mouse kidney M-1 cells were cultivated in DMEM containing 5% FCS and 5 µM dexamethasone for 10 to 12 days on polyester transwell filters. Filters were inserted into a teflon-coated well-plate which fit into the ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode with the software package Lab View for data acquisition and analysis. The transepithelial electrical resistance (TEER) was determined by the application of voltage steps of ±5 mV every 5 sec. Compounds were administered at a final concentration of 3 µM or at increasing concentrations (1-3-10 µM) to the apical solution. At the end of each experiment the amiloride sensitive I_SC was measured by adding 3 µM amiloride to the apical compartment. Results are expressed as inhibition in percent of the amiloride effect or as $IC_{50}$.

With the example compounds given above, the following $IC_{50}$ values were determined in the Ussing Chamber assay:

| | Example | | | | | | | | | |
|---|---|---|---|---|---|---|---|---|---|---|
| | 1.01 | 1.02 | 1.03 | 2.01 | 2.02 | 2.03 | 2.04 | 2.05 | 2.06 | 2.07 |
| $IC_{50}$ [nM] | 10 | 10 | 8 | 1 | 2 | 1 | 3 | 3 | 1 | 3 |

Permeability in CALU-3 Cells:

Permeability measurements across polarized, confluent CALU-3 cell monolayers grown on permeable filter supports are used to provide information on the potential of a compound to pass the lung epithelium. Apparent permeability coefficients (Papp) of the compounds across the CALU-3 cell monolayers are measured (pH 7.4, 37° C.) in apical-to-basal (AB) and basal-to-apical (BA) transport direction. AB permeability (Papp, AB) represents drug absorption from the lung lumen into the blood and BA permeability (Papp, BA) drug transport from the blood into the lung lumen mainly via passive permeability since Calu-3 cells as well as lung epithelial cells do not express efflux transporters like P-gp, while uptake transporters may be expressed.

CALU-3 cells ($1-2 \times 10^5$ cells/1 cm² area) are seeded on filter inserts (Costar transwell polycarbonate filters, 0.4 µm pore size) and cultured (for 10-12 days DMEM) until tight monolayers are formed. Compounds of interest are dissolved in appropriate solvent (DMSO, 10 mM stock solution). Stock solutions are diluted with HTP-4 buffer (128.13 mM NaCl, 5.36 mM KCl, 1 mM MgSO4, 1.8 mM CaCl2, 4.17 mM $NaHCO_3$, 1.19 mM Na2HPO4×7H2O, 0.41 mM NaH2PO4×H2O, 15 mM HEPES, 20 mM glucose, 0.25% BSA, pH 7.4) to prepare the transport solutions (10 µM compound, final DMSO<=0.5%). The transport solution (TL) is applied to the apical or basolateral donor side for measuring A-B or B-A permeability (3 filter replicates), respectively. The receiver side contains the same buffer as the donor side. After 30 min of accommodation, samples are collected at the start t0=0 min and at the end of the experiment tn=90 min from the donor and at 0, 30, 60, and 90 min also from the receiver chamber. Volume removed is replenished by HTP-4 buffer. The compound concentration in the samples is measured by HPLC-MS/MS or scintillation counting. The permeability coefficient (Papp) and efflux ratio are calculated according to: Papp [cm/s]=(concentration receiver [nM]*volume receiver [mL]/time interval [sec])*(1/filter area)*(1/donor concentration [nM]).

With example compounds given above, the following permeability values were determined in the CALU-3 cells assay:

| | Example | | | | | | |
|---|---|---|---|---|---|---|---|
| | 1.01 | 1.02 | 1.03 | 2.01 | 2.04 | 2.05 | 2.06 |
| Papp, AB [$10^{-6}$ cm/s] | 0.8 | 0.6 | 0.4 | 0.2 | <0.7 | 0.4 | <1 |
| Papp, BA [$10^{-6}$ cm/s] | 0.3 | 0.3 | 0.1 | 0.5 | 0.4 | 0.1 | 0.2 |

Indications

As has been found, the compounds of formula (I) are characterized by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, allergic diseases of the airways, or dry eyes.

Particular mention should be made of the prevention and treatment of diseases of the airways and of the lung which are accompanied by increased mucus production, inflammation and/or obstructive diseases of the airways. Examples include acute, allergic or chronic bronchitis, chronic obstructive pulmonary disease (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Combinations

The compounds of formula (I) may be used on their own or in conjunction with other active substances of formula (I) according to the invention. If desired the compounds of formula (I) may also be used in combination with other pharmacologically active substances.

Therefore the invention further relates to medicament combinations which preferably contain, besides one or more compounds of formula (I) or a salt thereof, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Formulations

Suitable forms for administration are for example inhalable powders or aerosols. The content of the pharmaceutically effective compound(s) in each case should be in the range from 0.2 to 50 wt %, preferably 0.5 to 25 wt % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 3 to 7 using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The invention claimed is:
1. A compound of formula (I),

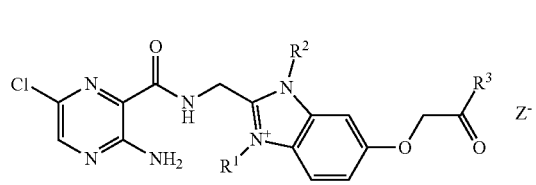

wherein
$R^1$ and $R^2$ are independently ethyl, 2-hydroxyethyl, 2-tetrahydrofuranylmethyl or 4-tetrahydropyranylmethyl;
$R^3$ is a moiety $NR^aR^b$, wherein $R^a$ and $R^b$ are independently hydrogen, $C_1$-$C_4$-alkyl or 1-(2-ethoxyethyl)piperidin-4-yl, wherein $C_1$-$C_4$-alkyl may carry 1 or 2 substituents selected from the group consisting of: hydroxyl, amino, $C_1$-$C_4$-alkylamino, di-$C_1$-$C_4$-alkylamino, (dimethylphosphinoyl)methoxy, 4-(dimethylphosphinoyl)phenyl, 6-methyl-3-hydroxy-pyridin-2-yl and the oxyanion of 6-methyl-3-hydroxy-pyridin-2-yl, provided that at least one of $R^a$ and $R^b$ is different from hydrogen,
or wherein $R^a$ and $R^b$ together with the nitrogen they are attached to form a heterocyclic moiety selected from the group consisting of: piperidine and 1-oxothiomorpholinyl, wherein the heterocyclic moiety may carry 1 or 2 $NH_2$ substituents; and
$Z^-$ is selected from the group consisting of: chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate and p-toluenesulfonate,
or $Z^-$ may be absent if $R^a$ or $R^b$ is $C_1$-$C_4$-alkyl and carries the oxyanion of 6-methyl-3-hydroxy-pyridin-2-yl;
or a pharmaceutically acceptable salt thereof.

2. The compound according to claim 1, wherein at least one of $R^1$ and $R^2$ is ethyl; or a pharmaceutically acceptable salt thereof.

3. The compound according to claim 2, wherein both of $R^1$ and $R^2$ are ethyl; or a pharmaceutically acceptable salt thereof.

4. The compound according to claim 1, wherein $Z^-$ is chloride, formate, or trifluoroacetate; or a pharmaceutically acceptable salt thereof.

5. The compound according to claim 1, wherein $R^3$ is

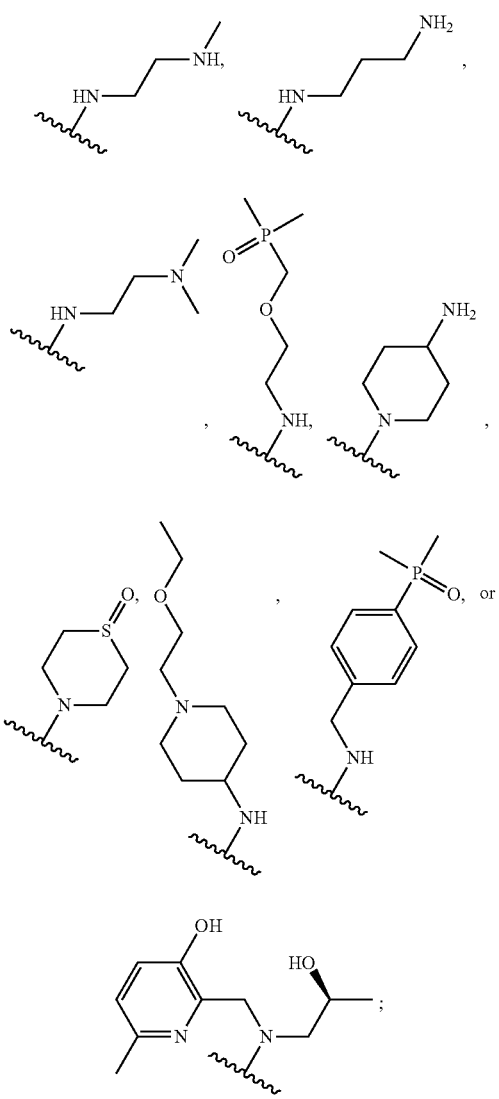

or a pharmaceutically acceptable salt thereof.

6. The compound according to claim 1, selected from the group consisting of

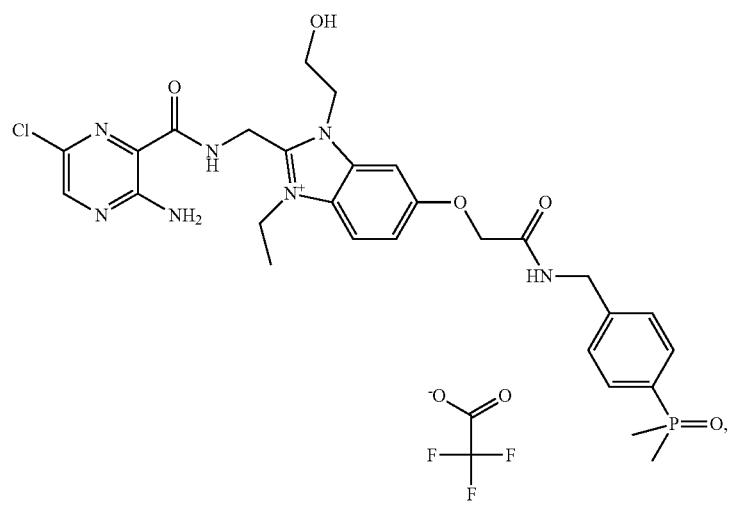
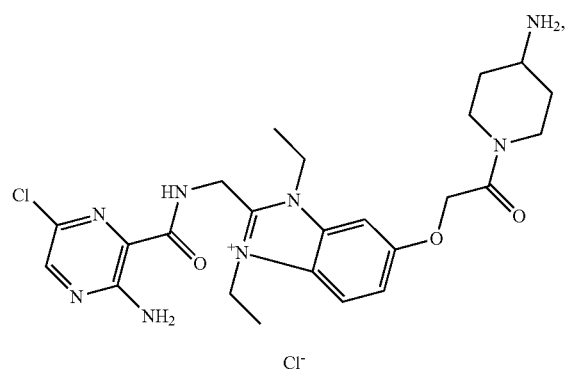
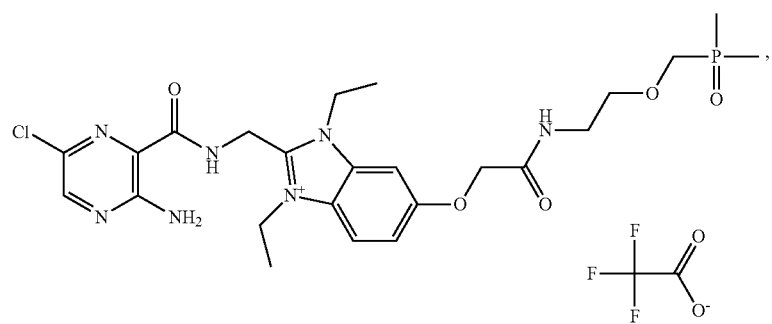
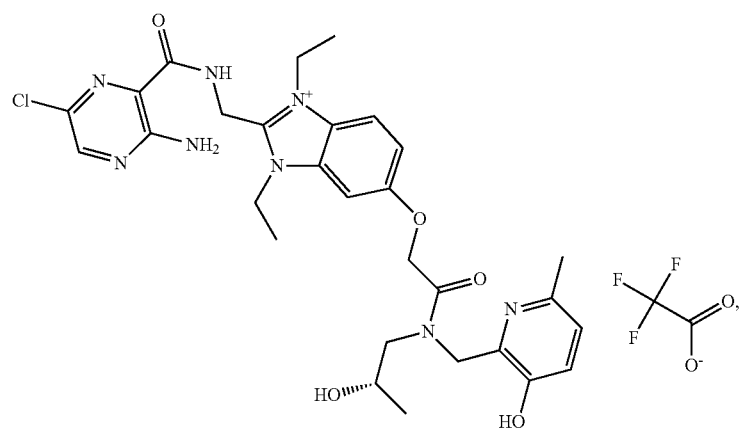

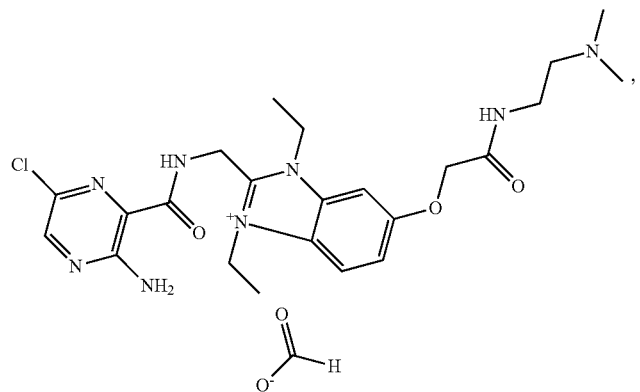
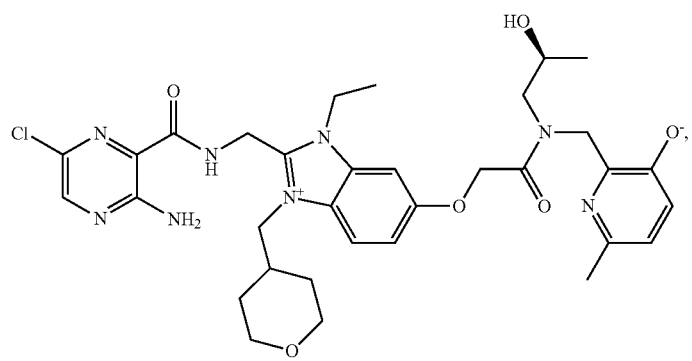
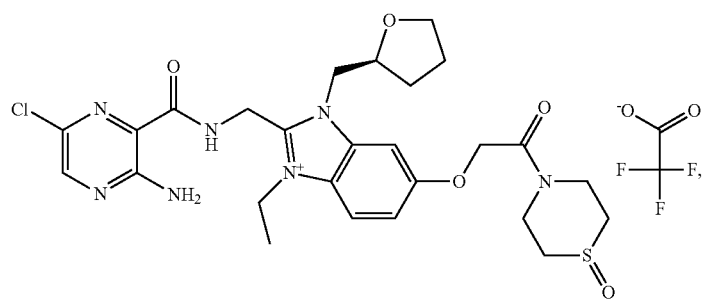
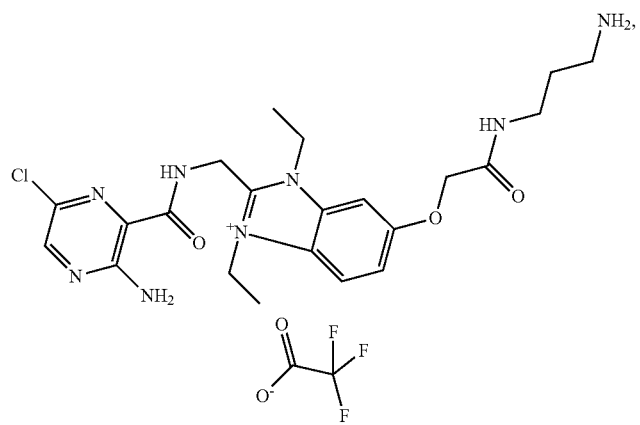

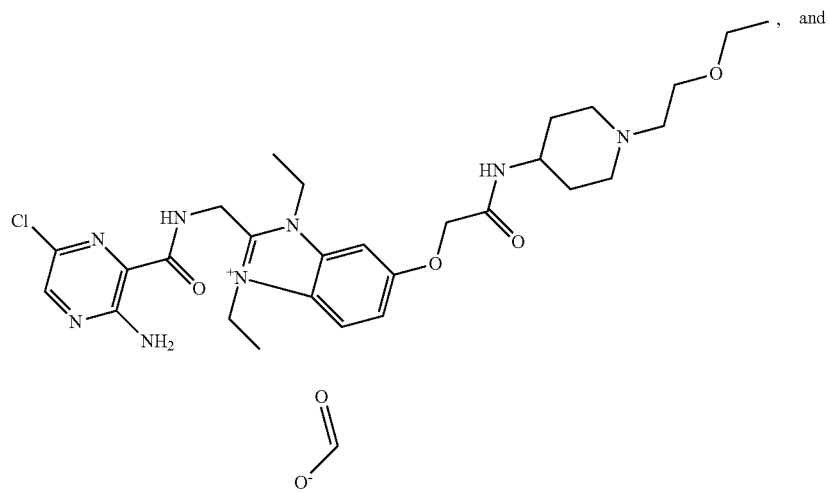

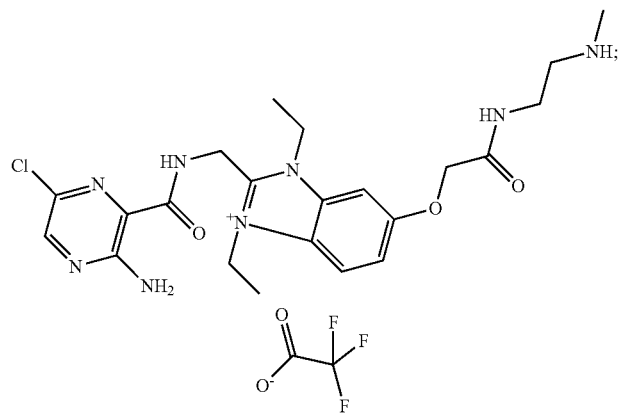

or a pharmaceutically acceptable salt thereof.

7. A pharmaceutical composition comprising at least one compound according to claim 1 or a pharmaceutically acceptable salt thereof and a pharmaceutically acceptable carrier.

8. The pharmaceutical composition according to claim 7, wherein the composition further comprises as further active substances, one or more compounds selected from the group consisting of: ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, correctors of the cystic fibrosis transmembrane regulator (CFTR) and CFTR potentiators.

9. The compound according to claim 1, which is:

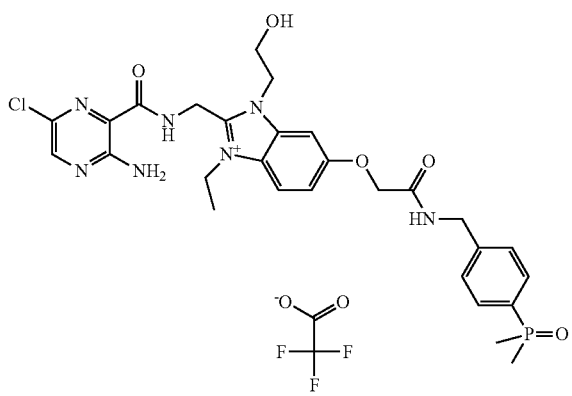

or a pharmaceutically acceptable salt thereof.

10. The compound according to claim 1, which is:
11. The compound according to claim 1, which is:
12. The compound according to claim 1, which is:
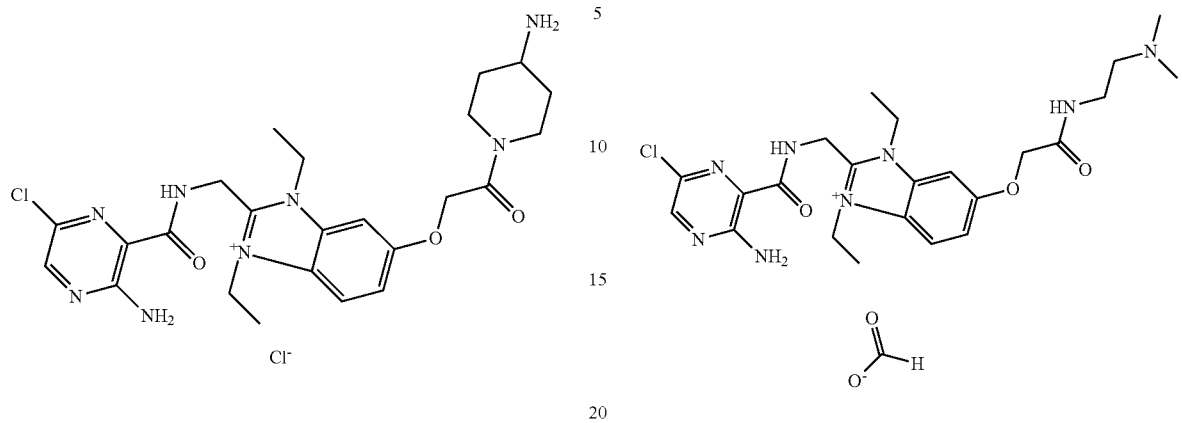
or a pharmaceutically acceptable salt thereof.
13. The compound according to claim 1, which is:
14. The compound according to claim 1, which is:
15. The compound according to claim 1, which is:
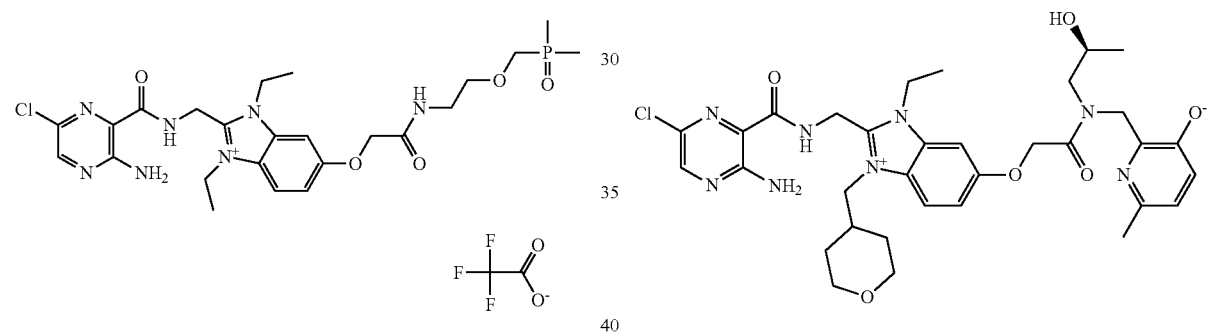
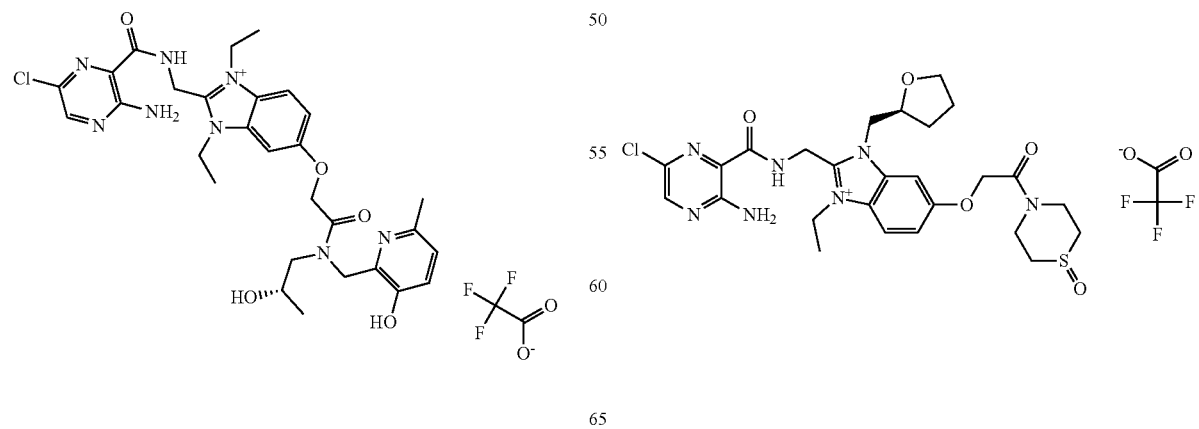
or a pharmaceutically acceptable salt thereof.

16. The compound according to claim 1, which is:

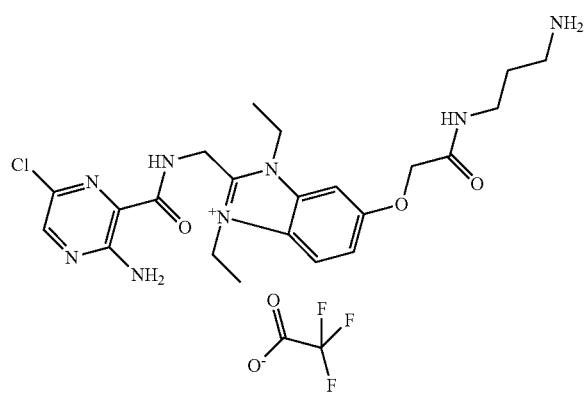 [SMILES: CCn1c(CNC(=O)c2nc(Cl)cnc2N)[n+](CC)c2ccc(OCC(=O)NCCCN)cc21 ; O=C([O-])C(F)(F)F]

or a pharmaceutically acceptable salt thereof.

17. The compound according to claim 1, which is:

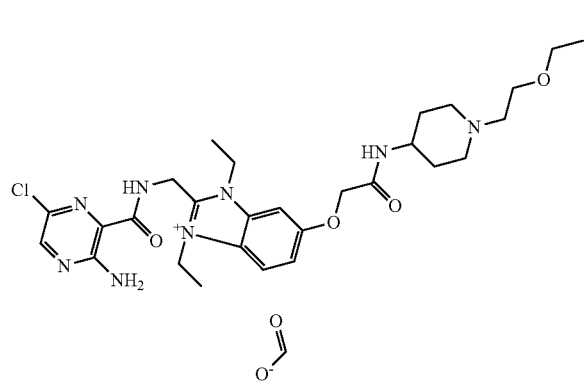

or a pharmaceutically acceptable salt thereof.

18. The compound according to claim 1, which is:

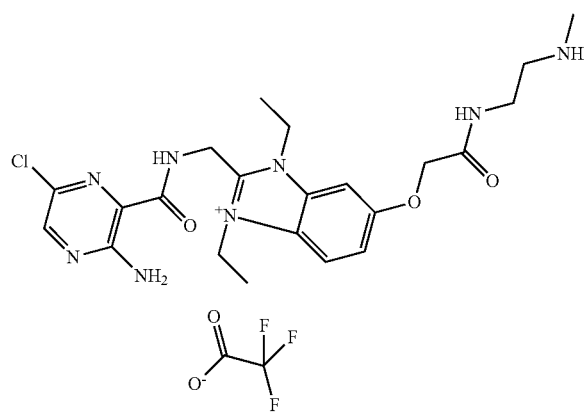 [SMILES: CCn1c(CNC(=O)c2nc(Cl)cnc2N)[n+](CC)c2ccc(OCC(=O)NCCNC)cc21 ; O=C([O-])C(F)(F)F]

or a pharmaceutically acceptable salt thereof.

19. A pharmaceutically acceptable salt of the following parent compound:

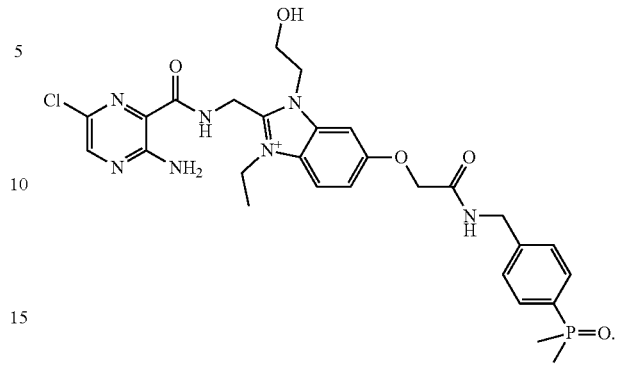

20. A pharmaceutically acceptable salt of the following parent compound:

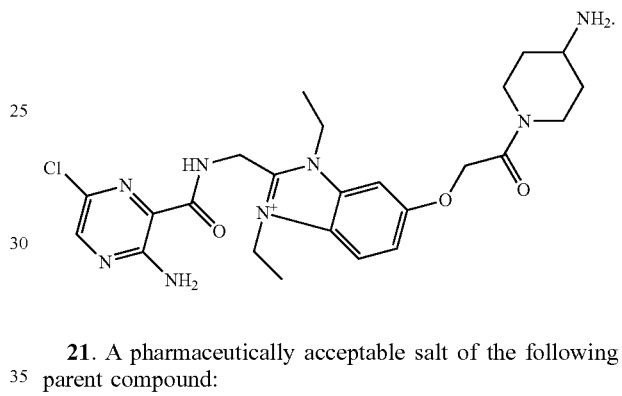

21. A pharmaceutically acceptable salt of the following parent compound:

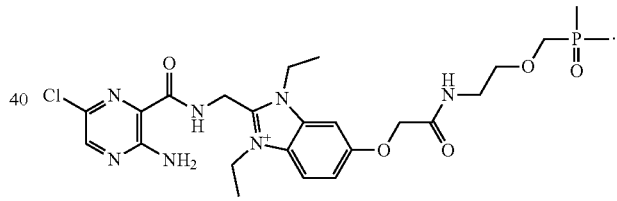

22. A pharmaceutically acceptable salt of the following parent compound:

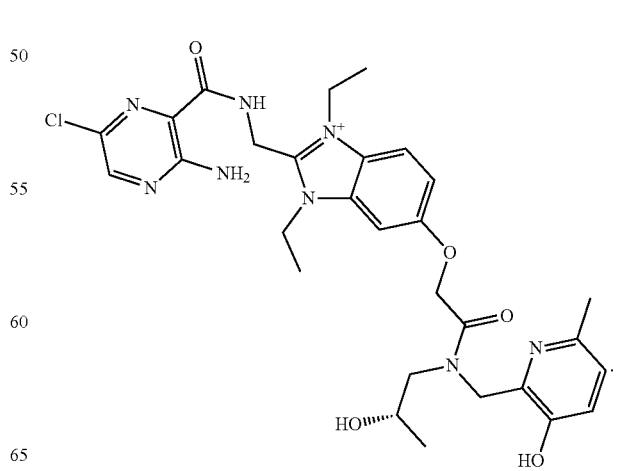

23. A pharmaceutically acceptable salt of the following parent compound:

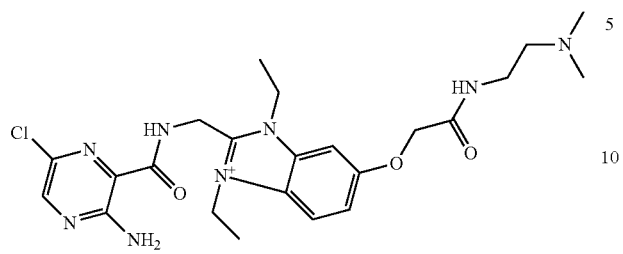

24. A pharmaceutically acceptable salt of the following parent compound:

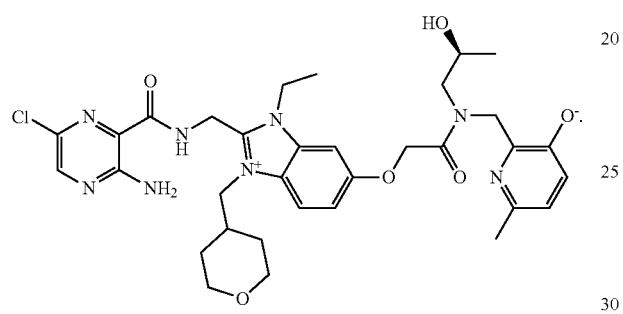

25. A pharmaceutically acceptable salt of the following parent compound:

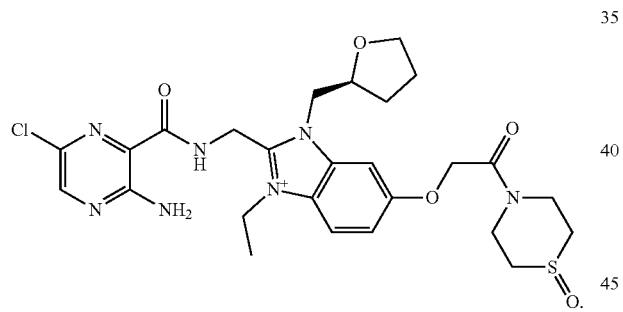

26. A pharmaceutically acceptable salt of the following parent compound:

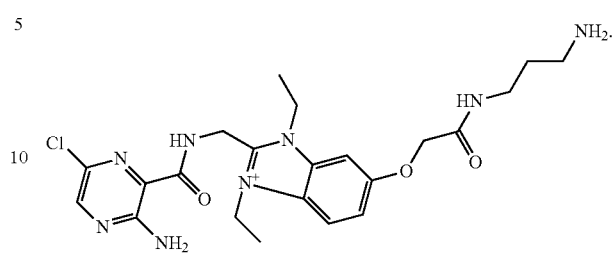

27. A pharmaceutically acceptable salt of the following parent compound:

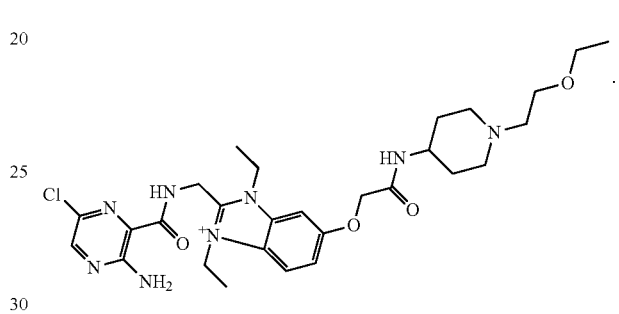

28. A pharmaceutically acceptable salt of the following parent compound:

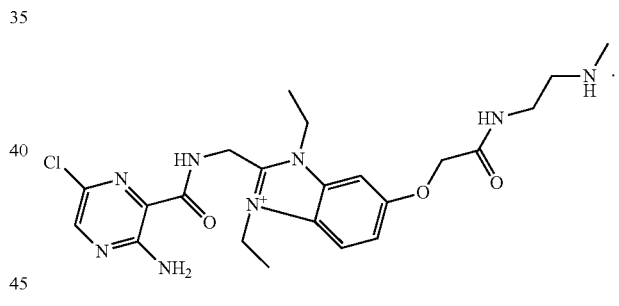

* * * * *